(12) United States Patent
Alig et al.

(10) Patent No.: US 6,548,694 B2
(45) Date of Patent: Apr. 15, 2003

(54) N-(4-CARBAMIMIDOYL-PHENYL)-GLYCINE DERIVATIVES

(75) Inventors: Leo Alig, Magden (CH); Katrin Groebke Zbinden, Basel (CH); Kurt Hilpert, Hofstetten (CH); Holger Kuehne, Grenzach-Wyhlen (DE); Ulrike Obst, Grenzach-Wyhlen (DE); Hans Peter Wessel, Heitersheim (DE)

(73) Assignee: Hoffman-La Roche Inc., Nutley, NJ (US)

( * ) Notice: Subject to any disclaimer, the term of this patent is extended or adjusted under 35 U.S.C. 154(b) by 121 days.

(21) Appl. No.: 09/858,535

(22) Filed: May 16, 2001

(65) Prior Publication Data

US 2002/0004608 A1 Jan. 10, 2002

(30) Foreign Application Priority Data

May 23, 2000 (EP) .............................. 00110881

(51) Int. Cl.[7] ............................. C07C 229/00
(52) U.S. Cl. ................ 560/35; 562/440; 558/394
(58) Field of Search .................. 560/35; 562/440; 558/394

(56) References Cited

U.S. PATENT DOCUMENTS 6,140,353 A    10/2000   Ackermann et al.

FOREIGN PATENT DOCUMENTS

EP     1078917     2/2001

WO     0035858   *  6/2000

* cited by examiner

*Primary Examiner*—Paul J. Killos
(74) *Attorney, Agent, or Firm*—George W. Johnston; John F. Parise

(57) ABSTRACT

N-(4-carbamimidoyl-phenyl)-glycine derivatives have the formula:

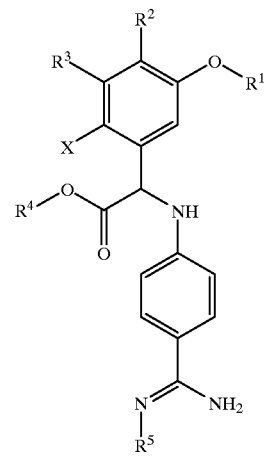

I wherein X and $R^1$ to $R^5$ are as defined herein, and includes hydrates or solvates and/or physiologically acceptable salts thereof and/or physiologically acceptable esters thereof.

132 Claims, No Drawings

N-(4-CARBAMIMIDOYL-PHENYL)-GLYCINE DERIVATIVES

BACKGROUND OF THE INVENTION

The subject invention relates to novel N-(4-carbamimidoyl-phenyl)-glycine derivatives.

SUMMARY OF THE INVENTION

The subject invention provides compounds of the formula:

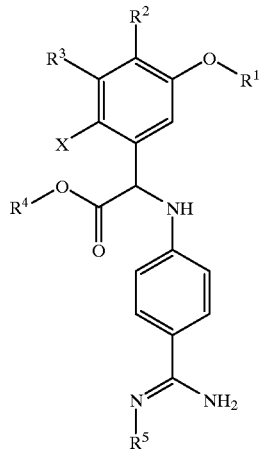

I wherein $R^1$ is alkyl;

$R^2$ is hydrogen, hydroxyalkoxy, alkoxycarbonyloxyalkoxy, or halogenalkoxycarbonyloxyalkoxy;

$R^3$ is hydrogen, alkoxy, or heterocycloalkyloxy;

$R^4$ is hydrogen or the residue of an ester group which is cleavable under physiological conditions;

$R^5$ is hydrogen, hydroxy, alkoxycarbonyl, halogenalkoxycarbonyl, aryloxycarbonyl, arylalkoxycarbonyl, alkoxyalkoxycarbonyl, cycloalkyloxycarbonyl, alkynyloxycarbonyl, 5-methyl-2-oxo-[1,3]dioxol-4-ylmethoxycarbonyl, arylcarbonyloxy, alkylaminocarbonyloxy, arylaminocarbonyloxy, alkylcarbonyl, arylcarbonyl, heteroarylcarbonyl, or arylaminocarbonyl; and X is F, Cl, or Br;

or a hydrate or solvates thereof, or a physiologically acceptable salt thereof or a physiologically acceptable ester thereof, with the provisio that the compound of formula I is not selected from the group consisting of:

(RS)-(4-carbamimidoyl-phenylamino)-(3,5-diethoxy-2-fluoro-phenyl)-acetic acid ethyl ester, (RS)-(4-carbamimidoyl-phenylamino)-(3,5-diethoxy-2-fluoro-phenyl)-acetic acid, (RS)-(4-carbamimidoyl-phenylamino)-(2-fluoro-3,5-dimethoxy-phenyl)-acetic acid, and (RS)-(4-carbamimidoyl-phenylamino)-(2-fluoro-3,5-dimethoxy-phenyl)-acetic acid ethyl ester.

Certain preferred compounds are where $R^1$ is ethyl or where only one of $R^2$ and $R^3$ is hydrogen. Other compounds are where $R^2$ is hydrogen, or hydroxyalkoxy, or 2-hydroxy-ethoxy, or alkoxycarbonyloxyalkoxy, or halogenalkoxycarbonyloxyalkoxy, or alkoxycarbonyloxyalkoxy, or halogenalkoxycarbonyloxyalkoxy, for exampe 2-(2,2,2-trichloro-ethoxycarbonyloxy)-ethoxy.

$R^3$ can be hydrogen, or alkoxy, for example ethoxy, or heterocycloalkyloxy, for example tetrahydrofuran-3-yloxy. It is also preferred where $R^4$ is hydrogen, alkyl, or aryl-alkyl. Where $R^4$ is alkyl, preferred groups include ethyl, iso-propyl, butyl, or iso-butyl. A preferred aryl-alkyl is benzyl.

For $R^5$, hydrogen, hydroxy, ethoxycarbonyl, 2,2,2-trichloro-ethoxycarbonyl, methoxycarbonyl, 4-fluoro-phenyloxycarbonyl, benzyloxycarbonyl, 2-methoxy-ethoxycarbonyl, 2-isopropyl-5-methyl-cyclohexyloxycarbonyl, prop-2-ynyloxycarbonyl, 5-methyl-2-oxo-[1,3]dioxol-4-ylmethoxycarbonyl, benzoyloxy, ethylaminocarbonyloxy, phenylaminocarbonyloxy, benzoyl, 3-fluoro-benzoyl, 4-fluoro-benzoyl, 2,4-difluoro-benzoyl, 3,4-dimethoxy-benzoyl, 3,5-dimethoxy-benzoyl, 4-methyl-benzoyl, 4-trifluoromethyl-benzoyl, phenylaminocarbonyl, or isobu-toxycarbonyl are preferred. While each of these substituents is useful, another grouping is where $R^5$ is alkoxycarbonyl, halogenalkoxycarbonyl, aryloxycarbonyl, arylalkoxycarbonyl, alkoxyalkoxycarbonyl, cycloalkyloxycarbonyl, alkynyloxycarbonyl, 5-methyl-2-oxo-[1,3]dioxol-4-ylmethoxycarbonyl, arylcarbonyloxy, alkylaminocarbonyloxy, arylaminocarbonyloxy, alkylcarbonyl, arylcarbonyl, heteroarylcarbonyl, or arylaminocarbonyl. A further subset is where $R^5$ is alkoxycarbonyl, halogenalkoxycarbonyl, alkoxyalkoxycarbonyl, cycloalkyloxycarbonyl, alkynyloxycarbonyl, alkylaminocarbonyloxy, or alkylcarbonyl. $R^5$ may also be 2,2,2-trichloro-ethoxycarbonyl, or alkylaminocarbonyloxy, or a substituent selected from the group consisting of aryloxycarbonyl, arylalkoxycarbonyl, arylaminocarbonyloxy, arylcarbonyl, and arylaminocarbonyl. Specific favored $R^5$ substituents include benzoyl, or alkylaminocarbonyloxy, or arylcarbonyloxy or arylaminocarbonyloxy, or 5-methyl-2-oxo-[1,3]dioxol-4-ylmethoxycarbonyl, or heteroarylcarbonyl.

While the halogens recited above are all effective as X, flourine is currently preferred.

The subject invention further provides compounds according to claim 1, wherein the compound is of the formula:

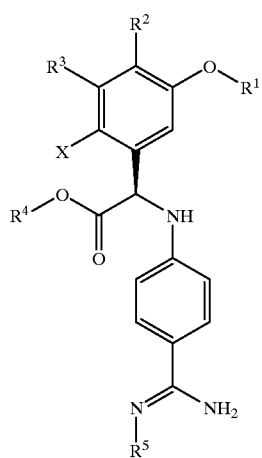

wherein $R^1$, $R^2$, $R^3$, $R^4$, $R^5$, and X are as defined above.

Other convenient groupings are where $R^3$ is hydrogen or heterocycloalkyloxy, $R^4$ is aryl-alkyl, and $R^5$ is hydroxy, alkoxycarbonyl, halogenalkoxycarbonyl, aryloxycarbonyl, arylalkoxycarbonyl, alkoxyalkoxycarbonyl, cycloalkyloxycarbonyl, alkynyloxycarbonyl, 5-methyl-2-oxo-[1,3]dioxol-4-ylmethoxycarbonyl, arylcarbonyloxy, alkylaminocarbonyloxy, arylaminocarbonyloxy, alkylcarbonyl, arylcarbonyl, heteroarylcarbonyl, or arylaminocarbonyl. X is conveniently Cl, or Br.

The subject invention also provides compounds of the formula:

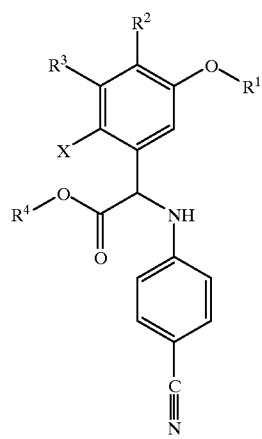

wherein
$R^1$ is alkyl;
$R^2$ is hydrogen, hydroxyalkoxy, alkoxycarbonyloxyalkoxy, or halogenalkoxycarbonyloxyalkoxy;
$R^3$ is hydrogen, alkoxy, or heterocycloalkyloxy;
$R^4$ is hydrogen or the residue of an ester group which is cleavable under physiological conditions; and
X is F, Cl, or Br.

Although various combinations of $R^1$, $R^2$, $R^3$, $R^4$, $R^5$ and X have been set out above, all combinations of these substituents are possible and are intended to be covered by this description as if specifically written out.

DETAILED DESCRIPTION OF THE PREFERRED EMBODIMENTS

The subject invention will now be described in terms of its preferred embodiments. These embodiments are set foth to aid in understanding the invention but are not to be construed as limiting.

The invention is concerned with novel N-(4-carbamimidoyl-phenyl)-glycine derivatives of the formula I

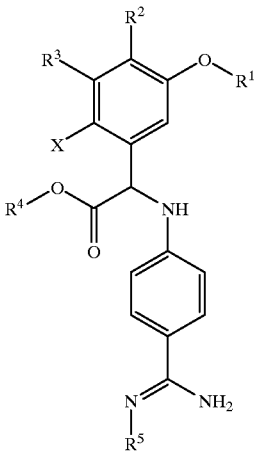

wherein
$R^1$ represents alkyl,
$R^2$ represents hydrogen, hydroxyalkoxy, alkoxycarbonyloxyalkoxy, or halogenalkoxycarbonyloxyalkoxy,
$R^3$ represents hydrogen, alkoxy, or heterocycloalkyloxy,
$R^4$ represents hydrogen or the residue of an ester group which is cleavable under physiological conditions;
$R^5$ represents hydrogen, hydroxy, alkoxycarbonyl, halogenalkoxycarbonyl, aryloxycarbonyl, arylalkoxycarbonyl, alkoxyalkoxycarbonyl, cycloalkyloxycarbonyl, alkynyloxycarbonyl, 5-methyl-2-oxo-[1,3]dioxol-4-ylmethoxycarbonyl, arylcarbonyloxy, alkylaminocarbonyloxy, arylaminocarbonyloxy, alkylcarbonyl, arylcarbonyl, heteroarylcarbonyl, or arylaminocarbonyl,
X represents F, Cl, or Br,
as well as hydrates or solvates and/or physiologically acceptable salts thereof and/or physiologically acceptable esters thereof,
with the provisio that said compound of formula I is not selected from the group consisting of:

(RS)-(4-carbamimidoyl-phenylamino)-(3,5-diethoxy-2-fluoro-phenyl)-acetic acid ethyl ester,
(RS)-(4-carbamimidoyl-phenylamino)-(3,5-diethoxy-2-fluoro-phenyl)-acetic acid,
(RS)-(4-carbamimidoyl-phenylamino)-(2-fluoro-3,5-dimethoxy-phenyl)-acetic acid, and
(RS)-(4-carbamimidoyl-phenylamino)-(2-fluoro-3,5-dimethoxy-phenyl)-acetic acid ethyl ester.

Further, the invention is concerned with a process for the manufacture of the above compounds, pharmaceutical preparations which contain such compounds as well as the use of these compounds for the production of pharmaceutical preparations.

Examples of physiologically usable salts of these compounds of formula I are salts with physiologically compatible mineral acids, such as hydrochloric acid, sulphuric acid, sulphurous acid or phosphoric acid; or with organic acids, such as methanesulphonic acid, p-toluenesulphonic acid, acetic acid, trifluoroacetic acid, citric acid, fumaric acid, maleic acid, tartaric acid, succinic acid or salicylic acid. The term "physiologically acceptable salts" refers to such compounds.

Examples of physiologically acceptable esters are esters of the compounds of formula I, in which hydroxy groups have been converted to the corresponding esters with inorganic or organic acids such as nitric acid, sulphuric acid, phosphoric acid, citric acid, formic acid, maleic acid, acetic acid, succinic acid, tartaric acid, methanesulphonic acid, p-toluenesulphonic acid and the like, which are non toxic to living organisms. The term "physiologically acceptable esters" refers to such compounds.

The compounds of formula I can be solvated, especially hydrated. The terms "solvates" and "hydrates" refer to compounds of formula 1 which additionally comprise solvent molecules or, in the case of hydrates, water molecules respectively. The hydration can take place in the course of the manufacturing process or can occur gradually as a consequence of hygroscopic properties of an initially anhydrous compound of formula I.

The compounds of formula I have at least one asymmetric C atom and can therefore exist as an enantiomeric mixture, diastereomeric mixture or as optically pure compounds. Compounds of formula I can exist in tautomeric forms and the invention encompasses all such tautomeric forms.

In the scope of the present invention "alkyl", alone or in combination with other groups, such as in alkoxy, alkoxycarbonyl etc., denotes a straight-chain or branched hydrocarbon residue containing 1–6, preferably 1–4 carbon atoms, such as, methyl, ethyl, propyl, iso-propyl, butyl, sec-butyl, tert-butyl and iso-butyl. Alkyl groups can be substituted, e.g. with one ore more halogen atoms, preferrably with chlorine, e.g. 2,2,2-trichloroethyl. Such groups are referred to as "halogenalkyl". Alkyl groups can also be substituted with other groups such as e.g. hydroxy, e.g. hydroxyethyl.

The term "alkoxy" stands for the group alkyl-O- with alkyl as defined above, e.g. methoxy, ethoxy, n-propoxy, iso-propoxy, n-butoxy, iso-butoxy.

The term "alkynyl", alone or in combination with other groups, stands for a straight-chain or branched hydrocarbon residue containing a triple bond and up to 6, preferably up to 4 C-atoms such as e.g. ethynyl, butynyl or prop-2-ynyl.

The term "cycloalkyl" stands for a cyclic alkyl group of three to six carbon atoms, e.g. cyclopropyl, cyclobutyl, cyclopentyl and cyclohexyl. Such cyclic alkyl groups can optionally be substituted by one ore more substituents such as e.g. alkyl, halogen, or alkoxy with alkyl being preferred.

The term "cycloalkoxy" or "cycloalkyloxy" denotes a cycloalkyl group which is bonded via an oxy (—O—) group, such as e.g. cyclopentyloxy or cyclohexyloxy.

The term "heterocycloalkyl" stands for a cyclic alkyl group of three to six carbon atoms which can contain 1 or 2 atoms selected from nitrogen, oxygen or sulphur such as e.g. tetrahydrofuran, pyrrolidine, morpholine, with tetrahydrofuran being preferred. Heterocycloalkyl groups can exhibit a substitution pattern as described for cycloalkyl.

The term "aryl", alone or in combination, such as in aryloxy, arylalkyl etc. denotes a carbocyclic, aromatic residue such as phenyl, naphthyl or indanyl, preferably phenyl and naphthyl, especially phenyl, which can be substituted, e.g. by halogen, such as bromine, fluorine or chlorine, alkyl, such as methyl, ethyl, propyl or butyl, halogenalkyl, such as trifluoromethly, alkoxy, such as methoxy, ethoxy or propoxy, hydroxy, nitro, amino, mono- or di-alkyl-amino, phenyl, phenoxy, COOH or COO-alkyl, such as $COOCH_3$ or $COOC_2H_5$. Preferred substituents are alkoxy, halogen, or alkyl, with fluorine being more preferred. Examples of arylalkyl groups are benzyl, phenethyl, mono- or dimethoxy-benzyl, aminobenzyl or nitrobenzy, with benzyl being preferred, examples of aryloxy groups are phenoxy or methoxycarbonyl-phenoxy, with phenoxy being preferred and examples of arylalkyloxy groups are benzyloxy, methoxy-benzyloxy and phenethoxy, with benzyloxy being preferred.

The term "heteroaryl" refers to an aromatic 5- or 6-membered ring which can contain 1 or 2 atoms selected from nitrogen, oxygen or sulphur such as furyl, pyridyl, 1,2-, 1,3- and 1,4-diazinyl, thiophenyl, isoxazolyl, oxazolyl or imidazolyl. A heteroaryl group may have a substitution pattern as described earlier in connection with the term "aryl".

The term "halogen" stands for fluorine, chlorine, bromine and iodine, preferably fluorine and chlorine and more preferably fluorine.

Examples of ester groups cleavable under physiological conditions denoted by $R^4$ are alkyl; hydroxyalkyl, such as e.g. hydroxyethyl; aryl-alkyl, morpholinoethyl; tetrahydropyranyl; alkoxycarbonyl-alkyl, such as tert.-butoxycarbonylmethyl (pivoxyl); alkoxycarbonyloxyalkyl, such as 1-(ethoxycarbonyloxy)ethyl, hexyloxycarbonyloxyalkyl (hexetil) and 1-isopropyloxycarbonyloxy)ethyl (proxetil); alkylcarbonyloxyalkyl, such as 1-acetoxyethyl (axetil), 1-(pivaloyloxy)ethyl and 1-(cyclohexylacetoxy) ethyl; dialkylaminocarbonylmethylene; morpholino-4-ylcarbonylmethylene. Preferred ester groups are methyl, ethyl, iso-propyl, butyl, iso-butyl or benzyl.

In detail, the present invention relates to compounds of formula I

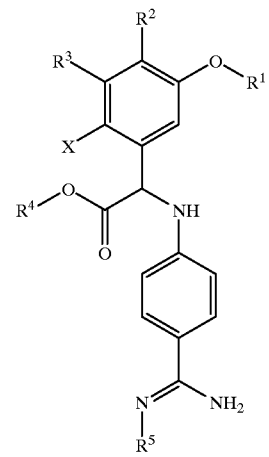

I wherein
 $R^1$ represents alkyl,
 $R^2$ represents hydrogen, hydroxyalkoxy, alkoxycarbonyloxyalkoxy, or halogen alkoxycarbonyloxyalkoxy,
 $R^3$ represents hydrogen, alkoxy, or heterocycloalkyloxy,
 $R^4$ represents hydrogen or the residue of an ester group which is cleavable under physiological conditions;
 $R^5$ represents hydrogen, hydroxy, alkoxycarbonyl, halogenalkoxycarbonyl, aryloxycarbonyl, arylalkoxycarbonyl, alkoxyalkoxycarbonyl, cycloalkyloxycarbonyl, alkynyloxycarbonyl, 5-methyl-2-oxo-[1,3]dioxol-4-ylmethoxycarbonyl, arylcarbonyloxy, alkylaminocarbonyloxy, arylaminocarbonyloxy, alkylcarbonyl, arylcarbonyl, heteroarylcarbonyl, or arylaminocarbonyl, X represents F, Cl, or Br, as well as hydrates or solvates and/or physiologically acceptable salts thereof and/or physiologically acceptable esters thereof, with the provisio that said compound of formula I is not selected from the group consisting of:

(RS)-(4-carbamimidoyl-phenylamino)-(3,5-diethoxy-2-fluoro-phenyl)-acetic acid ethyl ester,
(RS)-(4-carbamimidoyl-phenylamino)-(3,5-diethoxy-2-fluoro-phenyl)-acetic acid,
(RS)-(4-carbamimidoyl-phenylamino)-(2-fluoro-3,5-dimethoxy-phenyl)-acetic acid, and
(RS)-(4-carbamimidoyl-phenylamino)-(2-fluoro-3,5-dimethoxy-phenyl)-acetic acid ethyl ester.

Compounds of formula I as well as physiologically acceptable salts thereof and/or physiologically acceptable esters thereof are preferred, with the compounds of formula I being particularly preferred.

Preferred compounds of formula I are those, wherein only one of $R^2$ and $R^3$ represents hydrogen. Another preferred embodiment of the present invention are compounds as described above, wherein $R^1$ represents ethyl.

In a further preferred embodiment the invention relates to compounds as described above in which $R^2$ represents hydrogen, 2-hydroxy-ethoxy, or 2-(2,2,2-trichloro-ethoxycarbonyloxy)-ethoxy. Compounds in which $R^2$ represents hydrogen are preferred and such in which $R^2$ represents 2-hydroxy-ethoxy are also preferred. Compounds in which $R^3$ represents hydrogen are preferred, as well as compounds in which $R^3$ represents ethoxy and compounds in which $R^3$ represents tetrahydrofuran-3-yloxy.

The invention embraces especially compounds in accordance with the above definitions in which $R^4$ represents hydrogen, alkyl or aryl-alkyl, with hydrogen, ethyl, isopropyl, butyl, iso-butyl or benzyl being preferred, with hydrogen being more preferred and with ethyl also being more preferred.

Moreover, the invention relates especially to compounds as defined above in which $R^5$ represents hydrogen, hydroxy, ethoxycarbonyl, 2,2,2-trichloro-ethoxycarbonyl, methoxycarbonyl, 4-fluoro-phenyloxycarbonyl, benzyloxycarbonyl, 2-methoxy-ethoxycarbonyl, 2-isopropyl-5-methyl-cyclohexyloxycarbonyl, prop-2-ynyloxycarbonyl, 5-methyl-2-oxo-[1,3]dioxol-4-ylmethoxycarbonyl, benzoyloxy, ethylaminocarbonyloxy, phenylaminocarbonyloxy, benzoyl, 3-fluoro-benzoyl, 4-fluoro-benzoyl, 2,4-difluoro-benzoyl, 3,4-dimethoxy-benzoyl, 3,5-dimethoxy-benzoyl, 4-methyl-benzoyl, 4-trifluoromethyl-benzoyl, phenylaminocarbonyl, or isobutoxy-carbonyl. Compounds as defined above wherein $R^5$ is hydrogen are particularly preferred as well as compounds in which $R^5$ represents hydroxy, compounds in which $R^5$ represents benzoyl, and compounds in which $R^5$ represents 2,2,2-trichloro-ethoxycarbonyl. Another preferred embodiment relates to compounds in which X represents fluorine.

In context with the present invention, compounds according to the definitions given above characterised by formula Ia

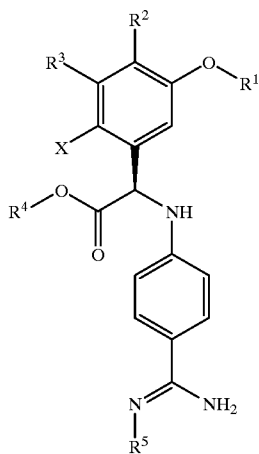

wherein $R^1$, $R^2$, $R^3$, $R^4$, $R^5$, and X have the significances given above are also preferred.

In particular, preferred compounds are the compounds of formula I described in the examples as individual compounds in the form of the free acids, their esters as well as hydrates or solvates and physiologically usable salts thereof.

Preferred individual compounds are those selected from the group consisting of:

(RS)-(4-Carbamimidoyl-phenylamino)-[5-ethoxy-2-fluoro-4-(2-hydroxy-ethoxy)-phenyl]-acetic acid ethyl ester hydrochloride,
(RS)-(4-Carbamimidoyl-phenylamino)-[5-ethoxy-2-fluoro-4-(2-hydroxy-ethoxy)-phenyl]-acetic acid,
(S)-(4-Carbamimidoyl-phenylamino)-[5-ethoxy-2-fluoro-4-(2-hydroxy-ethoxy)-phenyl]-acetic acid,
(R)-(4-Carbamimidoyl-phenylamino)-[5-ethoxy-2-fluoro-4-(2-hydroxy-ethoxy)-phenyl]-acetic acid,
(RS)-[5-Ethoxy-2-fluoro-4-(2-hydroxy-ethoxy)-phenyl]-[4-(N-hydroxycarbamimidoyl)-phenylamino]-acetic acid ethyl ester,
(S)-[5-Ethoxy-2-fluoro-4-(2-hydroxy-ethoxy)-phenyl]-[4-(N-hydroxycarbamimidoyl)-phenylamino]-acetic acid ethyl ester,
(R)-[5-Ethoxy-2-fluoro-4-(2-hydroxy-ethoxy)-phenyl]-[4-(N-hydroxycarbamimidoyl)-phenylamino]-acetic acid ethyl ester,
(RS)-[5-Ethoxy-2-fluoro-4-(2-hydroxy-ethoxy)-phenyl]-[4-(N-hydroxycarbamimidoyl)-phenylamino]-acetic acid sodiumchloride,
(RS)-[4-(Amino-ethoxycarbonylimino-methyl)-phenylamino]-[5-ethoxy-2-fluoro-4-(2-hydroxy-ethoxy)-phenyl]-acetic acid ethyl ester,
(RS)-{4-[Amino-(2,2,2-trichloro-ethoxycarbonylimino)-methyl]-phenylamino}-{5-ethoxy-2-fluoro-4-[2-(2,2,2-trichloro-ethoxycarbonyloxy)-ethoxy]-phenyl}-acetic acid ethyl ester,
(RS)-{4-[Amino-(2,2,2-trichloro-ethoxycarbonylimino)-methyl]-phenylamino}-[5-ethoxy-2-fluoro-4-(2-hydroxy-ethoxy)-phenyl]-acetic acid ethyl ester,
(S)-{4-[Amino-(2,2,2-trichloro-ethoxycarbonylimino)-methyl]-phenylamino}-[5-ethoxy-2-fluoro-4-(2-hydroxy-ethoxy)-phenyl]-acetic acid ethyl ester,
(R)-{4-[Amino-(2,2,2-trichloro-ethoxycarbonylimino)-methyl]-phenylamino}-[5-ethoxy-2-fluoro-4-(2-hydroxy-ethoxy)-phenyl]-acetic acid ethyl ester,
(RS)-[4-(Amino-methoxycarbonylimino-methyl)-phenylamino]-[5-ethoxy-2-fluoro-4-(2-hydroxy-ethoxy)-phenyl]-acetic acid ethyl ester, (RS)-{4-[Amino-(4-fluoro-phenoxycarbonylimino)-methyl]-phenylamino}-[5-ethoxy-2-fluoro-4-(2-hydroxy-ethoxy)-phenyl]-acetic acid ethyl ester,
(RS)-[4-(Amino-benzyloxycarbonylimino-methyl)-phenylamino]-[5-ethoxy-2-fluoro-4-(2-hydroxy-ethoxy)-phenyl]-acetic acid ethyl ester,
(RS)-{4-[Amino-(2-methoxy-ethoxycarbonylimino)-methyl]-phenylamino}-[5-ethoxy-2-fluoro-4-(2-hydroxy-ethoxy)-phenyl]-acetic acid ethyl ester,
{4-[Amino-[1R-(2S-isopropyl-5R-methyl-cyclohexyl)oxycarbonylimino]-methyl]-phenylamino}-α(RS)-[5-ethoxy-2-fluoro-4-(2-hydroxy-ethoxy)-phenyl]-acetic acid ethyl ester,
(RS)-[4-(Amino-prop-2-ynyloxycarbonylimino-methyl)-phenylamino]-[5-ethoxy-2-fluoro-4-(2-hydroxy-ethoxy)-phenyl]-acetic acid ethyl ester,
(RS)-{4-[Amino-(5-methyl-2-oxo-[1,3]dioxol-4-ylmethoxycarbonylimino)-methyl]-phenylamino}-[5-ethoxy-2-fluoro-4-(2-hydroxy-ethoxy)-phenyl]-acetic acid ethyl ester,
(R,S)-α-[[4-[[(Benzoyloxy)amino]iminomethyl]phenyl]amino]-5-ethoxy-2-fluoro-4-(2-hydroxyethoxy)-benzeneacetic acid ethyl ester,
(R,S)-5-Ethoxy-α-[[4-[[[[(ethylamino)carbonyl]oxy]amino]iminomethyl]phenyl]amino]-2-fluoro-4-(2-hydroxyethoxy)-benzeneacetic acid ethyl ester,
(R,S)-5-Ethoxy-2-fluoro-4-(2-hydroxyethoxy)-α-[[4-[imino[[[(phenylamino)carbonyl]oxy]amino]methyl]phenyl]amino]-benzeneacetic acid ethyl ester,
(RS)-{4-[Amino-(4-fluoro-benzoylimino)-methyl]-phenylamino}-[5-ethoxy-2-fluoro-4-(2-hydroxy-ethoxy)-phenyl]-acetic acid ethyl ester,
(RS)-[4-(Amino-benzoylimino-methyl)-phenylamino]-[5-ethoxy-2-fluoro-4-(2-hydroxy-ethoxy)-phenyl]-acetic acid ethyl ester,
(S)-[4-(Amino-benzoylimino-methyl)-phenylamino]-[5-ethoxy-2-fluoro-4-(2-hydroxy-ethoxy)-phenyl]-acetic acid ethyl ester,
(R)-[4-(Amino-benzoylimino-methyl)-phenylamino]-[5-ethoxy-2-fluoro-4-(2-hydroxy-ethoxy)-phenyl]-acetic acid ethyl ester,
(RS)-[4-(Amino-phenylcarbamoylimino-methyl)-phenylamino]-[5-ethoxy-2-fluoro-4-(2-hydroxy-ethoxy)-phenyl]-acetic acid ethyl ester,
(RS)-[5-Ethoxy-2-fluoro-4-(2-hydroxy-ethoxy)-phenyl]-[4-(N-hydroxycarbamimidoyl)-phenylamino]-acetic acid butyl ester,
(S)-[5-Ethoxy-2-fluoro-4-(2-hydroxy-ethoxy)-phenyl]-[4-(N-hydroxycarbamimidoyl)-phenylamino]-acetic acid butyl ester,
(R)-[5-Ethoxy-2-fluoro-4-(2-hydroxy-ethoxy)-phenyl]-[4-(N-hydroxycarbamimidoyl)-phenylamino]-acetic acid butyl ester,
(RS)-[5-Ethoxy-2-fluoro-4-(2-hydroxy-ethoxy)-phenyl]-[4-(N-hydroxycarbamimidoyl)-phenylamino]-acetic acid isopropyl ester,
(S)-[5-Ethoxy-2-fluoro-4-(2-hydroxy-ethoxy)-phenyl]-[4-(N-hydroxycarbamimidoyl)-phenylamino]-acetic acid isopropyl ester,
(R)-[5-Ethoxy-2-fluoro-4-(2-hydroxy-ethoxy)-phenyl]-[4-(N-hydroxycarbamimidoyl)-phenylamino]-acetic acid isopropyl ester,
(RS)-[5-Ethoxy-2-fluoro-4-(2-hydroxy-ethoxy)-phenyl]-[4-(N-hydroxycarbamimidoyl)-phenylamino]-acetic acid benzyl ester,
(S)-[5-Ethoxy-2-fluoro-4-(2-hydroxy-ethoxy)-phenyl]-[4-(N-hydroxycarbamimidoyl)-phenylamino]-acetic acid benzyl ester,
(R)-[5-Ethoxy-2-fluoro-4-(2-hydroxy-ethoxy)-phenyl]-[4-(N-hydroxycarbamimidoyl)-phenylamino]-acetic acid benzyl ester,
(RS)-[5-Ethoxy-2-fluoro-4-(2-hydroxy-ethoxy)-phenyl]-[4-(N-hydroxycarbamimidoyl)-phenylamino]-acetic acid isobutyl ester,
(S)-[5-Ethoxy-2-fluoro-4-(2-hydroxy-ethoxy)-phenyl]-[4-(N-hydroxycarbamimidoyl)-phenylamino]-acetic acid isobutyl ester,
(R)-[5-Ethoxy-2-fluoro-4-(2-hydroxy-ethoxy)-phenyl]-[4-(N-hydroxycarbamimidoyl)-phenylamino]-acetic acid isobutyl ester,
(RS)-{4-[Amino-(2,4-difluoro-benzoylimino)-methyl]-phenylamino}-[5-ethoxy-2-fluoro-4-(2-hydroxy-ethoxy)-phenyl]-acetic acid ethyl ester,
(RS)-{4-[Amino-(3,5-dimethoxy-benzoylimino)-methyl]-phenylamino}-[5-ethoxy-2-fluoro-4-(2-hydroxy-ethoxy)-phenyl]-acetic acid ethyl ester,
(RS)-{4-[Amino-(3,4-dimethoxy-benzoylimino)-methyl]-phenylamino}-[5-ethoxy-2-fluoro-4-(2-hydroxy-ethoxy)-phenyl]-acetic acid ethyl ester,
(RS)-{4-[Amino-(3-fluoro-benzoylimino)-methyl]-phenylamino}-[5-ethoxy-2-fluoro-4-(2-hydroxy-ethoxy)-phenyl]-acetic acid ethyl ester,
(RS)-{4-[Amino-(4-trifluoromethyl-benzoylimino)-methyl]-phenylamino}-[5-ethoxy-2-fluoro-4-(2-hydroxy-ethoxy)-phenyl]-acetic acid ethyl ester,
(RS)-{4-[Amino-(4-methyl-benzoylimino)-methyl]-phenylamino}-[5-ethoxy-2-fluoro-4-(2-hydroxy-ethoxy)-phenyl]-acetic acid ethyl ester,
(R)-(4-Carbamimidoyl-phenylamino)-(3,5-diethoxy-2-fluoro-phenyl)-acetic acid,
(S)-(4-Carbamimidoyl-phenylamino)-(3,5-diethoxy-2-fluoro-phenyl)-acetic acid,
(RS)-(3,5-Diethoxy-2-fluoro-phenyl)-[4-(N-hydroxycarbamimidoyl)-phenylamino]-acetic acid ethyl ester,
(R)-(3,5-Diethoxy-2-fluoro-phenyl)-[4-(N-hydroxycarbamimidoyl)-phenylamino]-acetic acid ethyl ester,
(S)-(3,5-Diethoxy-2-fluoro-phenyl)-[4-(N-hydroxycarbamimidoyl)-phenylamino]-acetic acid ethyl ester,
(RS)-(3,5-Diethoxy-2-fluoro-phenyl)-[4-(N-hydroxycarbamimidoyl)-phenylamino]-acetic acid,
(R)-(3,5-Diethoxy-2-fluoro-phenyl)-[4-(N-hydroxycarbamimidoyl)-phenylamino]-acetic acid,
(S)-(3,5-Diethoxy-2-fluoro-phenyl)-[4-(N-hydroxycarbamimidoyl)-phenylamino]-acetic acid,
(RS)-[4-(Amino-ethoxycarbonylimino-methyl)-phenylamino]-(3,5-diethoxy-2-fluoro-phenyl)-acetic acid ethyl ester,
(RS)-{4-[Amino-(4-fluoro-phenoxycarbonylimino)-methyl]-phenylamino}-(3,5-diethoxy-2-fluoro-phenyl)-acetic acid ethyl ester,
(RS)-{4-[Amino-(2,2,2-trichloro-ethoxycarbonylimino)-methyl]-phenylamino}-(3,5-diethoxy-2-fluoro-phenyl)-acetic acid ethyl ester,
(RS)-{4-[Amino-(5-methyl-2-oxo-[1,3]dioxol-4-ylmethoxycarbonylimino)-methyl]-phenylamino}-(3,5-diethoxy-2-fluoro-phenyl)-acetic acid ethyl ester,
(RS)-[4-(Amino-methoxycarbonylimino-methyl)-phenylamino]-(3,5-diethoxy-2-fluoro-phenyl)-acetic acid ethyl ester,
(RS)-[4-(Amino-phenoxycarbonylimino-methyl)-phenylamino]-(3,5-diethoxy-2-fluoro-phenyl)-acetic acid ethyl ester, (RS)-[4-(Amino-isobutoxycarbonylimino-methyl)-phenylamino]-(3,5-diethoxy-2-fluoro-phenyl)-acetic acid ethyl ester,
(RS)-{4-[Amino-(4-fluoro-benzoylimino)-methyl]-phenylamino}-(3,5-diethoxy-2-fluoro-phenyl)-acetic acid ethyl ester,
(RS)-(3,5-Diethoxy-2-fluoro-phenyl)-[4-(N-hydroxycarbamimidoyl)-phenylamino]-acetic acid butyl ester,
(RS)-(3,5-Diethoxy-2-fluoro-phenyl)-[4-(N-hydroxycarbamimidoyl)-phenylamino]-acetic acid isopropyl ester,
(RS)-[5-Ethoxy-2-fluoro-3-[(R)-tetrahydro-furan-3-yloxy]-phenyl]-[4-(N-hydroxycarbamimidoyl)-phenylamino]-acetic acid ethyl ester,
(R)-[5-Ethoxy-2-fluoro-3-[(R)-tetrahydro-furan-3-yloxy]-phenyl]-[4-(N-hydroxycarbamimidoyl)-phenylamino]-acetic acid ethyl ester,
(S)-[5-Ethoxy-2-fluoro-3-[(R)-tetrahydro-furan-3-yloxy)-phenyl]-[4-(N-hydroxycarbamimidoyl)-phenylamino]-acetic acid ethyl ester,
(RS)-(4-Carbamimidoyl-phenylamino)-[5-ethoxy-2-fluoro-3-[(R)-tetrahydro-furan-3-yloxy]-phenyl]-acetic acid ethyl ester hydrochloride, (RS)-(4-Carbamimidoyl-phenylamino)-[5-ethoxy-2-fluoro-3-[(R)-tetrahydro-furan-3-yloxy]-phenyl]-acetic acid,
(R)-(4-Carbamimidoyl-phenylamino)-[5-ethoxy-2-fluoro-3-[(R)-tetrahydro-furan-3-yloxy]-phenyl]-acetic acid,
(S)-(4-Carbamimidoyl-phenylamino)-[5-ethoxy-2-fluoro-3-[(R)-tetrahydro-furan-3-yloxy]-phenyl]-acetic acid,
(RS)-(4-Carbamimidoyl-phenylamino)-[5-ethoxy-2-fluoro-3-[(S)-tetrahydro-furan-3-yloxy]phenyl]-acetic acid ethyl ester hydrochloride,
(RS)-(4-Carbamimidoyl-phenylamino)-[5-ethoxy-2-fluoro-3-[(S)-tetrahydro-furan-3-yloxy]-phenyl]-acetic acid,
(R)-(4-Carbamimidoyl-phenylamino)-[5-ethoxy-2-fluoro-3-[(S)-tetrahydro-furan-3-yloxy]-phenyl]-acetic acid, and
(S)-(4-Carbamimidoyl-phenylamino)-[5-ethoxy-2-fluoro-3-[(S)-tetrahydro-furan-3-yloxy]-phenyl]-acetic acid.

Particularly preferred are those compounds selected from the group consisting of (R)-(4-Carbamimidoyl-phenylamino)-[5-ethoxy-2-fluoro-4-(2-hydroxy-ethoxy)-phenyl]-acetic acid,
(R)-(4-Carbamimidoyl-phenylamino)-(3,5-diethoxy-2-fluoro-phenyl)-acetic acid,
(R)-(4-Carbamimidoyl-phenylamino)-[5-ethoxy-2-fluoro-3-[(R)-tetrahydro-furan-3-yloxy]-phenyl]-acetic acid,
(R)-[5-Ethoxy-2-fluoro-4-(2-hydroxy-ethoxy)-phenyl]-[4-(N-hydroxycarbamimidoyl)-phenylamino]-acetic acid ethyl ester,
(R)-{4-[Amino-(2,2,2-trichloro-ethoxycarbonylimino)-methyl]-phenylamino}-[5-ethoxy-2-fluoro-4-(2-hydroxy-ethoxy)-phenyl]-acetic acid ethyl ester,
(R)-[4-(Amino-benzoylimino-methyl)-phenylamino]-[5-ethoxy-2-fluoro-4-(2-hydroxy-ethoxy)-phenyl]-acetic acid ethyl ester,
(R)-[5-Ethoxy-2-fluoro-4-(2-hydroxy-ethoxy)-phenyl]-[4-(N-hydroxycarbamimidoyl)-phenylamino]-acetic acid butyl ester,
(R)-[5-Ethoxy-2-fluoro-4-(2-hydroxy-ethoxy)-phenyl]-[4-(N-hydroxycarbamimidoyl)-phenylamino]-acetic acid isopropyl ester,
(R)-[5-Ethoxy-2-fluoro-4-(2-hydroxy-ethoxy)-phenyl]-[4-(N-hydroxycarbamimidoyl)-phenylamino]-acetic acid benzyl ester, and
(R)-[5-Ethoxy-2-fluoro-4-(2-hydroxy-ethoxy)-phenyl]-[4-(N-hydroxycarbamimidoyl)-phenylamino]-acetic acid isobutyl ester.

Other particularly preferred compounds are those selected from the group consisting of (R)-(4-carbamimidoyl-phenylamino)-[5-ethoxy-2-fluoro-4-(2-hydroxy-ethoxy)-phenyl]-acetic acid ethyl ester,
(R)-[5-ethoxy-2-fluoro-4-(2-hydroxy-ethoxy)-phenyl]-[4-(N-hydroxycarbamimidoyl)-phenylamino]-acetic acid, and
(RS)-[5-ethoxy-2-fluoro-3-[(S)-tetrahydro-furan-3-yloxy]-phenyl]-[4-(N-hydroxycarbamimidoyl)-phenylamino]-acetic acid ethyl ester.

Another preferred compound is (S)-(4-carbamimidoyl-phenylamino)-[5-ethoxy-2-fluoro-4-(2-hydroxy-ethoxy)-phenyl]-acetic acid ethyl ester.

Physiologically acceptable salts of the compounds individually mentioned above also constitute a preferred embodiment of the present invention.

Further preferred compounds in accordance with the definitions given above are those, wherein $R^3$ is not alkoxy if $R^5$ is hydrogen.

The invention further relates to a process for the manufacture of compounds of formula I, which process comprises converting the nitrile group in a compound of formula II

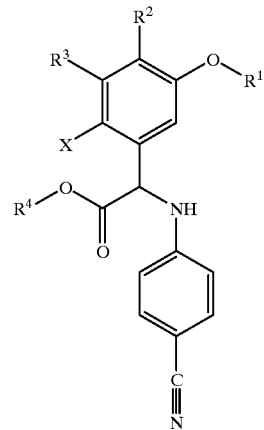

II wherein $R^1$, $R^2$, $R^3$, $R^4$ and X have the significances given above, into a carbamimidoyl group or into a N-hydroxycarbamimidoyl group and, if desired, modifying a reactive group present in an obtained compound of formula I and, if desired, converting a compound of formula I obtained into a physiologically compatible salt or converting a salt of a compound of formula I into the free acid or base.

Further the invention relates to compounds of formula I as defined above, when manufactured according to this process. In another embodiment the invention relates to compounds of formula II, wherein $R^1$, $R^2$, $R^3$, $R^4$ and X have the significances given above.

The conversion of the nitrile group in a compound of formula II into a carbamimidoyl group —C(NH)NH$_2$ or a N-hydroxy-carbamimidoyl group —C(NOH)NH$_2$ can be carried out according to methods known per se. For example, the conversion into a N-hydroxycarbamimidoyl group can be performed by dissolving a compound of formula II in a solvent, such as DMF, ethanol or methanol, treating the solution with hydroxylamine or a salt of hydroxylamine with an inorganic acid, such as hydroxylamine hydrochloride, and thereafter with a base, such as diisopropylethylamine or triethylamine, sodium hydride or sodium methanolate, conveniently at a temperature up to 80° C.

The conversion of the nitrile group into a carbamimidoyl group can be carried out e.g. by treating a compound of formula II in a solvent, such as ethanol or methanol, or a solvent mixture, such as chloroform and methanol or chloroform and ethanol, with a dry stream of hydrogen chloride, conveniently at a temperature below 10° C., thereafter treating the reaction solution with a solvent, such as diethyl ether, and filtering off the precipitated iminoether. The thus-obtained material is treated in a solvent, such as methanol or ethanol, either with gaseous ammonia or an ammonium salt, such as ammonium chloride, conveniently at a temperature up to 80° C. Alternatively, the solution containing the iminoether can be evaporated and the residue can be treated with gaseous ammonia or an ammonium salt in methanol or ethanol. In an analogous manner, the iminoether can be converted into a N-hydroxy-carbamimidoyl compound of formula I with hydroxylamine or a salt thereof in the presence of a base.

As modifications of functional groups present in a compound of formula I there come into consideration especially the conversion of a N-hydroxy-carbamimidoyl group into a carbamimidoyl group, the esterification of a carboxy group, the saponification of an ester group and the cleavage of an ether group, such as an arylalkyl ether group, e.g. the benzyl ether group. All of these reactions can be carried out according to methods known per se.

For the conversion of a N-hydroxy-carbamimidoyl group into a carbamimidoyl group, an amidoxime of formula I can be hydrogenated in a solvent, such as ethanol, methanol, dioxan, THF or glacial acetic acid, or a solvent mixture, such as ethanol and glacial acetic acid, with hydrogen and a catalyst, such as palladium, platinum or nickel. In so doing, other reactive groups present in the compound of formula I and reactive towards the reducing agent can be modified.

By reacting a compound of formula I in which $R^5$ represents hydrogen with a suitable chloroformic acid ester wherein a hydroxy or carboxy group can be present in protected form, in a solvent, such as dichloromethane, dioxane or DMF, or a solvent mixture, such as dichloromethane and water or ethyl acetate and water, in the presence of an organic base, such as pyridine or triethylamine, or an inorganic base, such as sodium hydroxide, sodium carbonate or potassium hydrogen carbonate, there is obtained the corresponding compound of formula I in which $R^5$ as described above represents alkoxycarbonyl, halogenalkoxycarbonyl, aryloxycarbonyl, arylalkoxycarbonyl, alkoxyalkoxycarbonyl, cycloalkyloxycarbonyl, alkynyloxycarbonyl or a similar group comprising an oxycarbonyl structure. Analogously, a compound of formula I in which $R^5$ represents hydrogen can be converted with a suitable p-nitrophenyl carbonate into the corresponding compound of formula I in which $R^5$ as described above represents a group comprising an oxycarbonyl structure. The reaction can e.g. be carried out by treating the p-nitrophenyl carbonate in THF and DMF firstly with N,N-diisopropylethylamine and then with a compound of formula I in which $R^5$ represents hydrogen.

By reacting a compound of formula I in which $R^5$ represents hydrogen with an acyl chloride, such as an aroyl chloride, there is obtained the corresponding compound of formula I in which $R^5$ as defined before represents an acyl group. The reaction can e.g. carried out by treating the acyl chloride in THF and DMF firstly with N,N-diisopropylethylamine and then with a compound of formula I in which $R^5$ represents hydrogen.

By reacting a compound of formula I in which $R^5$ represents hydroxy with an acyl halide there can be obtained a compound of formula I in which $R^5$ as defined above represents arylcarbonyloxy or a similar group comprising a carbonyloxy structure. The reaction can e.g. be carried out by treating the acyl chloride in THF and DMF firstly with N,N-diisopropylethylamine and then with a compound of formula I in which $R^5$ represents hydroxy.

By reacting a compound of formula I in which $R^5$ represents hydrogen with a suitable isocyanate there can be obtained a compound of formula I in which $R^5$ as described above represents a group comprising an aminocarbonyl structure. The reaction can be carried out by reacting a compound of formula I in which $R^5$ represents hydrogen with a suitable isocyanate in THF and DMF in the presence of triethylamine.

By reacting a compound of formula I in which $R^5$ represents hydroxy with a suitable isocyanate there can be obtained a compound of formula I in which $R^5$ as described above represents a group comprising an aminocarbonyloxy structure. The reaction can be carried out by reacting a compound of formula I in which $R^5$ represents hydroxy with a suitable isocyanate in THF.

The compounds of formula II can be prepared according to general methods known per se, e.g. as described hereinafter and/or as described in the Examples or in analogy to these methods. For example, an aldehyde of formula III

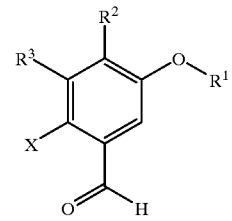

III in which $R^1$, $R^2$, $R^3$ and X have the significances given above, can be reacted with a p-aminobenzonitrile of formula IV

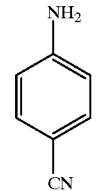

IV and benzylisonitrile, toluenesulfonylmethylisonitrile, or morpholinoethylisocyanide, and a primary alkanol such as methanol or ethanol, in the presence of boron trifluoride etherate. Hydrolysis of the resulting iminoether with water yields a compound of formula II in which $R^4$ represents methyl or ethyl. By hydrolysis of the ester group $R^4$, e.g. by treatment with LiOH in tetrahydrofuran, there is obtained a compound of formula II in which $R^4$ represents hydrogen.

Further reactions for the preparation of compounds of formula II:
By reaction of compounds of formula II in which $R^1$ together with the connecting oxygen atom and/or one or more of $R^2$ –$R^3$ represent hydroxy:
   with an alkylating agent such as an alkyl bromide, alkyl iodide or alkyl mesylate in the presence of a base such as potassium carbonate or caesium carbonate in a solvent such as DMF or acetone, or by a Mitsunobu reaction with an alcohol in the presence of DEAD, DIAD, or di-tert.-butyl-azodicarboxylate, and triphenylphosphine in a solvent such as THF or dioxane, there are obtained compounds of formula II in which the hydroxy group is converted to an alkoxy group.

Compounds of formula III are known per se. They can be obtained e.g. by reacting compounds of formula III in which $R^1$ together with the connecting oxygen atom and/or one or more of $R^2$–$R^3$:
represent a hydroxy group
  with an alkylating agent such as e.g. ethyl bromide in the presence of a base such as potassium carbonate oder caesium carbonate in a suitable solvent such as DMF or acetone, preferably at an elevated temperature, or
  in a Mitsunobu reaction with an alcohol in the presence of DEAD, DIAD, or di-tert.-butyl-azodicarboxylate, and triphenylphosphine in a solvent such as THF or dioxane, to give compounds of formula III in which the hydroxy group is substituted by an alkoxy group;
represent a silyloxy group
  with an alkylating agent such as e.g. an alkyl bromide in a suitable solvent such as e.g. DMF in the presence of potassium fluoride, to give compounds of formula III in which the silyloxy group is substituted by an alkoxy group.

Starting materials for the preparation of compounds of formula III are either commercially available or can be prepared by methods known in the art.

Insofar as their preparation is not described in the Examples, the compounds of formulae I, II, III and IV can be prepared according to analogous methods or according to the methods set forth above.

The compounds of formula I are active compounds and inhibit the formation of coagulation factors Xa, IXa and thrombin induced by factor VIIa and tissue factor or are derivatives which are converted under physiological conditions to such active compounds. These compounds consequently influence both platelet aggregation which is induced by these factors and plasmatic blood coagulation. They therefore inhibit the formation of thrombi and can be used for the control or prevention of diseases, such as thrombosis, apoplexy, cardiac infarction, inflammation and arteriosclerosis. Furthermore, these compounds have an effect on tumour cells and prevent metastases. They can therefore also be employed as antitumour agents.

Accordingly, the present invention also relates to pharmaceutical preparations comprising a compound as described above and a pharmaceutically acceptable carrier and/or adjuvant.

The invention likewise embraces compounds as described above for use as therapeutic active substances. The subject compounds can inhibit formation of clotting factors Xa, IXa and thrombin induced by factor VIIa and tissue factor. Such inhibitors can be used as therapeutic active substances for the treatment or prevention of thrombosis, apoplexy, cardiac infarction, inflammation and/or arteriosclerosis and/or as an antitumour agent.

In another preferred embodiment, the invention relates to a method for the therapeutic and/or prophylactic treatment of thrombosis, apoplexy, cardiac infarction, inflammation, arteriosclerosis and/or tumor, which method comprises administering a compound as defined above to a human being or animal.

The invention also embraces the use of a compound as defined above for the treatment or prophylaxis of thrombosis, apoplexy, cardiac infarction, inflammation, arteriosclerosis and/or tumor.

The invention also relates to the use of a compound as described above for the preparation of medicaments for the treatment or prevention of thrombosis, apoplexy, cardiac infarction, inflammation and arteriosclerosis or of antitumor agents. Such medicaments comprise a compound as described above.

The inhibition of the amidolytic activity of factor VIIa/tissue factor complex by the compounds in accordance with the invention can be demonstrated with the aid of a chromogenic peptide substrate as described hereinafter.

The measurements were carried out on microtitre plates at room temperature. To this end, 100 $\mu$l of a solution of 26 nM of tissue factor, 9 nM of soluble factor VIIa and 8 mM of calcium chloride were added to 25 $\mu$l of a solution of the inhibitor in a buffer [pH 7.5, 100 mM, comprising 0.14M NaCl, 0.1M N-(2-hydroxyethyl)piperazine-N'-(2-ethanesulphonic acid) (HEPES), 0.5 mg/l of fatty-acid-free BSA (bovine serum albumin) and 0.05% $NaN_3$] in each well of the plate. After an incubation time of 15 minutes the reaction was started by the addition of 50 $\mu$l of chromogenic substrate Chromozym-tPA (3.5 mM, $MeSO_2$-D-Phe-Gly-Arg-paranitroanilide) and the hydrolysis of the substrate was followed spectrophotometrically on a kinetic microtitre plate reader over 10 minutes. Using the plot of the inhibition curves, the Ki values were determined according to the method described in Biochem. J. 55, 1953, 170–171.

The activity of the low molecular weight substances can, moreover, be characterized in the "prothrombin time" (PT) clotting test. The substances are prepared as a 10 mM solution in DMSO or DMSO/0.1M HCl (DHCl) and thereafter made up to the desired dilution in the same solvent. Thereafter, 0.25 ml of human plasma (obtained from whole blood anticoagulated with 1/10 volume of 108 mM Na citrate) was placed in the instrument-specific sample container. In each case 5 $\mu$l of each dilution of the substance-dilution series was then mixed with the plasma provided. This plasma/inhibitor mixture was incubated at 37° C. for 2 minutes. Thereafter, there were pipetted to the semi-automatic device (ACL, Automated Coagulation Laboratory (Instrument Laboratory)) 50 $\mu$l of plasma/inhibitor mixture in the measurement container. The clotting reaction was initiated by the addition of 0.1 ml of Innovin® (recombinant human tissue factor combined with calcium buffer and synthetic phospholipids (Dade Behring®, Inc.). The time up to the fibrin cross-linking was determined photooptically from the ACL. The inhibitor concentration, which brought about a doubling of the PT clotting time, was determined by means of a graph.

The Ki value of the active compounds of the present invention preferably amounts to about 0.1 to 500 nM, especially about 0.1 to 150 nM. The PT values preferably amount to about 0.1 to 10 $\mu$M, especially to about 0.1 to 5 $\mu$M.

As mentioned earlier, medicaments containing a compound of formula I, a solvate or a salt thereof also form an object of the present invention, as does a process for the production of such medicaments which comprises bringing one or more of such compounds, solvates or salts and, if desired, other therapeutically useful substances into a galenical administration form. These medicaments can be administered orally, e.g. in the form of dragées, hard and soft gelatine capsules, solutions, emulsions or suspensions, or rectally, for example in the form of suppositories, or as a spray. However, administration can also be carried out parenterally, e.g. in the form of injection solutions.

For the production of tablets, coated tablets, dragées and hard gelatine capsules, the active ingredient can be mixed with pharmaceutically inert, inorganic or organic excipients. Suitable excipients for tablets, coated tablets, dragées and hard gelatine capsules are, for example, lactose, maize starch or derivatives thereof, talc, stearic acid or its salts. Suitable excipients for soft gelatine capsules are, for example, vegetable oils, waxes, fats, semi-solid and liquid polyols; depending on the nature of the active ingredient no excipients are, however, usually required in the case of soft gelatine capsules. Suitable excipients for the production of solutions and syrups are e.g. water, polyols, sucrose, invert sugar and glucose; suitable excipients for injection solutions are e.g. water, alcohols, polyols, glycerol and vegetable oils, and suitable excipients for suppositories are natural and hardened oils, waxes, fats, semi-liquid or liquid polyols. In addition, the pharmaceutical preparations can also contain preservatives, solubilizers, stabilizers, wetting agents, emulsifiers, sweeteners, colorants, flavorants, salts for varying the osmotic pressure, buffers, coating agents or antioxidants.

The dosage of the active ingredient for the control or prevention of the illnesses mentioned above can vary within wide limits and will, of course, be adapted to the individual requirements in each particular case. In general, in the case of oral or parenteral, e.g. intravenous or subcutaneous, administration, a dose of about 0.1 to 20 mg/kg, preferably about 0.6 to 5 mg/kg, per day should be adequate for adults, although the upper limit which has just been mentioned may be exceeded or the dose may be lower when this is shown to be indicated.

The following examples shall illustrate in more detail the present invention and preferred embodiments thereof but are not intended to limit the scope of the invention.

EXAMPLES

Example 1

1.1

To a solution of 2-bromo-4-fluorophenol (25.8 g) in DMF (100 ml) was added $K_2CO_3$ (20.5 g) and ethyl iodide (23.2 g). The mixture was stirred for 24 h at room temperature. Water (400 ml) was added and the mixture was extracted with hexane. The organic phase was washed with water, dried, filtered over a plug of silica gel and evaporated to yield 30.1 g of 2-bromo-1-ethoxy-4-fluoro-benzene as a colorless oil. MS: 220 ([M+H]$^+$).

1.2

The 2-bromo-1-ethoxy-4-fluoro-benzene (3.1 g) described in example 1.1 was dissolved in THF (25 ml). The solution was cooled to −75° C. and a solution of n-BuLi (9.73 ml, 1.6 M in hexane) was added slowly. The mixture was stirred for 30 min at −75° C. Trimethylborate (1.62 g) was added within 5 min. Acetic acid (1.27 g) and a 30% solution of $H_2O_2$ (1.51 g) were added sequentially. The mixture was stirred for 30 min at 0° C. and for 3 h at room temperature. Water was added and the mixture was extracted with ethyl acetate. The crude product was purified by column chromatography (n-hexane/ethyl acetate) to yield 1.77 g of 2-ethoxy-5-fluoro-phenol as a colorless oil. MS: 156 ([M]$^+$).

1.3

The 2-ethoxy-5-fluoro-phenol (14.3 g) described in example 1.2 was dissolved in trifluoroacetic acid (90 ml). This solution was slowly added to a solution of hexamethylene tetramine (25.7 g) in trifluoroacetic acid (90 ml) at 80° C. The mixture was stirred for 1 h at 80° C. and concentrated. Water (250 ml) was added and stirred for 10 min. The mixture was neutralized with $Na_2CO_3$ and extracted with ether. The crude product was purified by column chromatography (n-hexane/ethyl acetate) to yield 9.43 g of 5-ethoxy-2-fluoro-4-hydroxy-benzaldehyde as a yellow solid. MS: 184 ([M]$^+$).

1.4

The 5-ethoxy-2-fluoro-4-hydroxy-benzaldehyde (9.15 g) described in example 1.3 was dissolved in toluene (80 ml). Ethylene carbonate (5.25 g) and tetrabutylammonium iodide (1.83 g) were added and the mixture was heated to reflux for 22 h. The mixture was cooled to room temperature and filtered over a plug of silica gel. The product was eluted with hexane/ethyl acetate. The solvent was evaporated and the solid was washed with hot hexane to give 10.3 g of 5-ethoxy-2-fluoro-4-(2-hydroxy-ethoxy)-benzaldehyde as a slightly orange solid. MS: 228 ([M]$^+$).

1.5

The 5-ethoxy-2-fluoro-4-(2-hydroxy-ethoxy)-benzaldehyde (10.34 g) described in example 1.4 was dissolved in ethanol (160 ml). 4-Aminobenzonitrile (4.87 g) was added and stirred at room temperature. After 1 hour, 5.68 ml of morpholinoethyl isonitrile was added. The solution obtained was cooled to 0° C., then treated dropwise with 15.53 ml of boron trifluoride etherate in a manner such that the temperature did not exceed 5° C. The reaction mixture was stirred at 0° C. for 15 min and at room temperature for 1.5 h. Water (20 ml) was added and stirred overnight at room temperature. The crude product was isolated by extraction and purified by chromatography on silica gel and yielded 11.13 g of (RS)-(4-cyano-phenylamino)-[5-ethoxy-2-fluoro-4-(2-hydroxy-ethoxy)-phenyl]-acetic acid ethyl ester as a yellowish solid. MS: 425 ([M+Na]$^+$).

1.6

The (RS)-(4-cyano-phenylamino)-[5-ethoxy-2-fluoro-4-(2-hydroxy-ethoxy)-phenyl]-acetic acid ethyl ester (201 mg) described in example 1.5 was dissolved in a mixture of chloroform (1.9 ml) and ethanol (0.38 ml). The mixture was cooled to −10° C. and saturated with dry HCl gas. The flask was stoppered and stored overnight at 4° C. The mixture was concentrated to dryness. Ethanol (1.1 ml) and a solution of ammonia (2 M in EtOH, 0.5 ml) were added and the mixture was stirred at 65° C. for 2.5 h. The mixture was concentrated and the product was isolated by column chromatography ($CH_2Cl_2$/MeOH) to yield 182 mg of (RS)-(4-carbamimidoyl-phenylamino)-[5-ethoxy-2-fluoro-4-(2-hydroxy-ethoxy)-phenyl]-acetic acid ethyl ester hydrochloride as a colorless solid. MS: 420 ([M+H]$^+$).

This compound was separated into the enantiomers by preparative HPLC on a chiral stationary phase (Chiralpak AD) using heptane/ethanol/trifluoroacetic acid (60:40:0.2) as a mobile phase to give (S)-(4-carbamimidoyl-phenylamino)-[5-ethoxy-2-fluoro-4-(2-hydroxy-ethoxy)-phenyl]-acetic acid ethyl ester trifluoroacetate and (R)-(4-carbamimidoyl-phenylamino)-[5-ethoxy-2-fluoro-4-(2-hydroxy-ethoxy)-phenyl]-acetic acid ethyl ester trifluoroacetate as colorless solids. These compounds can be neutralised to give (S)-(4-carbamimidoyl-phenylamino)-[5-ethoxy-2-fluoro-4-(2-hydroxy-ethoxy)-phenyl]-acetic acid ethyl ester and (R)-(4-carbamimidoyl-phenylamino)-[5-ethoxy-2-fluoro-4-(2-hydroxy-ethoxy)-phenyl]-acetic acid ethyl ester respectively.

1.7

The (RS)-(4-carbamimidoyl-phenylamino)-[5-ethoxy-2-fluoro-4-(2-hydroxy-ethoxy)-phenyl]-acetic acid ethyl ester hydrochloride (172 mg) described in example 1.6 was suspended in THF (1.1 ml). A solution of NaOH (0.82 ml, 1 M in $H_2O$) was added and stirred for 30 min at 0° C. and for 40 min at room temperature. 1M HCl (0.41 ml) was added. The mixture was concentrated. The solid was washed with water and ether and dried to give 129 mg of (RS)-(4-carbamimidoyl-phenylamino)-[5-ethoxy-2-fluoro-4-(2-hydroxy-ethoxy)-phenyl]-acetic acid as a colorless solid. MS: 392 ([M+H]$^+$).

This compound was separated into the enantiomers by preparative HPLC on a chiral stationary phase (Chiralpak AD) using heptane/ethanol/trifluoroacetic acid (50:50:0.2) as a mobile phase to give after neutralization (S)-(4-carbamimidoyl-phenylamino)-[5-ethoxy-2-fluoro-4-(2-hydroxy-ethoxy)-phenyl]-acetic acid and (R)-(4-carbamimidoyl-phenylamino)-[5-ethoxy-2-fluoro-4-(2-hydroxy-ethoxy)-phenyl]-acetic acid as colorless solids.

1.8.

The (RS)-(4-cyano-phenylamino)-[5-ethoxy-2-fluoro-4-(2-hydroxy-ethoxy)-phenyl]-acetic acid ethyl ester (177 mg) described in example 1.5 was dissolved in a mixture of chloroform (1.7 ml) and ethanol (0.3 ml). The mixture was cooled to −10° C. and saturated with dry HCl gas. The flask was stoppered and stored overnight at 4° C. The mixture was concentrated to dryness. Ethanol (13 ml), hydroxylamine hydrochloride (61 mg) and triethylamine (222 mg) were added and the mixture was stirred at room temperature for 2 h. The product was isolated by extraction and column chromatography (CH$_2$Cl$_2$/MeOH) to yield 116 mg of (RS)-[5-ethoxy-2-fluoro-4-(2-hydroxy-ethoxy)-phenyl]-[4-(N-hydroxycarbamimidoyl)-phenylamino]-acetic acid ethyl ester as a colorless foam. MS: 436 ([M+H]$^+$).

This compound was separated into the enantiomers by preparative HPLC on a chiral stationary phase (Chiralpak AD) using heptane/ethanol/trifluoroacetic acid (75:25:0.2) as a mobile phase to give after neutralization (S)-[5-ethoxy-2-fluoro-4-(2-hydroxy-ethoxy)-phenyl]-[4-(N-hydroxycarbamimidoyl)-phenylamino]-acetic acid ethyl ester and (R)-[5-ethoxy-2-fluoro-4-(2-hydroxy-ethoxy)-phenyl]-[4-(N-hydroxycarbamimidoyl)-phenylamino]-acetic acid ethyl ester as colorless foams.

1.9

The (RS)-[5-ethoxy-2-fluoro-4-(2-hydroxy-ethoxy)-phenyl]-[4-(N-hydroxycarbamimidoyl)-phenylamino]-acetic acid ethyl ester (44 mg) described in example 1.8 was suspended in THF (0.9 ml). A 1 M solution of NaOH (0.101 ml) was added and the mixture was stirred for 30 min at 0° C. and for 2.5 h at room temperature. The mixture was neutralized with 1 M HCl and concentrated to give 42 mg of (RS)-[5-ethoxy-2-fluoro-4-(2-hydroxy-ethoxy)-phenyl]-[4-(N-hydroxycarbamimidoyl)-phenylamino]-acetic acid sodiumchloride as a colorless solid. MS: 408 ([M+H]$^+$).

This compound was separated into the enantiomers by HPLC on achiral stationary phase (Chiralpak AD) using n-hexane with 0.4% trifluoroacetic acid/ethanol (85:15) as a mobile phase to give, after neutralisation, (R)-[5-ethoxy-2-fluoro-4-(2-hydroxy-ethoxy)-phenyl]-[4-(N-hydroxycarbamimidoyl)-phenylamino]-acetic acid as colorless solid.

1.10

The (RS)-(4-carbamimidoyl-phenylamino)-[5-ethoxy-2-fluoro-4-(2-hydroxy-ethoxy)-phenyl]-acetic acid ethyl ester hydrochloride (100 mg) described in example 1.6 was dissolved in DMF (1 ml). At 0° C., ethyl chloroformate (24 mg) and triethylamine (67 mg) were added. The mixture was stirred for 1 h at 0° C. The product was isolated by extraction and column chromatography (CH$_2$Cl$_2$/acetone) to give 106 mg of (RS)-[4-(amino-ethoxycarbonylimino-methyl)-phenylamino]-[5-ethoxy-2-fluoro-4-(2-hydroxy-ethoxy)-phenyl]-acetic acid ethyl ester as a colorless foam. MS: 492 ([M+H]$^+$).

1.11

In analogy to example 1.10, the (RS)-(4-carbamimidoyl-phenylamino)-[5-ethoxy-2-fluoro-4-(2-hydroxy-ethoxy)-phenyl]-acetic acid ethyl ester hydrochloride described in example 1.6 was converted to (RS)-{4-[amino-(2,2,2-trichloro-ethoxycarbonylimino)-methyl]-phenylamino}-[5-ethoxy-2-fluoro-4-(2-hydroxy-ethoxy)-phenyl]-acetic acid ethyl ester by a reaction with 2,2,2-trichloroethyl chloroformate. MS: 596 ([M+H]$^+$) This compound was separated into the enantiomers by preparative HPLC on a chiral stationary phase (Chiralpak AD) using heptane/ethanol/diethylamine (60:40:0.2) as a mobile phase to give (S)-{4-[amino-(2,2,2-trichloro-ethoxycarbonylimino)-methyl]-phenylamino}-[5-ethoxy-2-fluoro-4-(2-hydroxy-ethoxy)-phenyl]-acetic acid ethyl ester and (R)-{4-[amino-(2,2,2-trichloro-ethoxycarbonylimino)-methyl]-phenylamino}-[5-ethoxy-2-fluoro-4-(2-hydroxy-ethoxy)-phenyl]-acetic acid ethyl ester. As a by-product, there was obtained (RS)-{4-[amino-(2,2,2-trichloro-ethoxycarbonylimino)-methyl]-phenylamino}-{5-ethoxy-2-fluoro-4-[2-(2,2,2-trichloro-ethoxycarbonyloxy)-ethoxy]-phenyl}-acetic acid ethyl ester. MS: 770.

1.12

In analogy to example 1.10, the (RS)-(4-carbamimidoyl-phenylamino)-[5-ethoxy-2-fluoro-4-(2-hydroxy-ethoxy)-phenyl]-acetic acid ethyl ester hydrochloride described in example 1.6 was converted to (RS)-[4-(amino-methoxycarbonylimino-methyl)-phenylamino]-[5-ethoxy-2-fluoro-4-(2-hydroxy-ethoxy)-phenyl]-acetic acid ethyl ester by a reaction with methyl chloroformate. MS: 478 ([M+H]$^+$)

1.13

In analogy to example 1.10, the (RS)-(4-carbamimidoyl-phenylamino)-[5-ethoxy-2-fluoro-4-(2-hydroxy-ethoxy)-phenyl]-acetic acid ethyl ester hydrochloride described in example 1.6 was converted to (RS)-{4-[amino-(4-fluoro-phenoxycarbonylimino)-methyl]-phenylamino}-[5-ethoxy-2-fluoro-4-(2-hydroxy-ethoxy)-phenyl]-acetic acid ethyl ester by a reaction with 4-fluorophenyl chloroformate.

1.14

In analogy to example 1.10, the (RS)-(4-carbamimidoyl-phenylamino)-[5-ethoxy-2-fluoro-4-(2-hydroxy-ethoxy)-phenyl]-acetic acid ethyl ester hydrochloride described in example 1.6 was converted to (RS)-[4-(Amino-benzyloxycarbonylimino-methyl)-phenylamino]-[5-ethoxy-2-fluoro-4-(2-hydroxy-ethoxy)-phenyl]-acetic acid ethyl ester by a reaction with benzyl chloroformate. MS: 554 ([M+H]$^+$).

1.15

In analogy to example 1.10, the (RS)-(4-carbamimidoyl-phenylamino)-[5-ethoxy-2-fluoro-4-(2-hydroxy-ethoxy)-phenyl]-acetic acid ethyl ester hydrochloride described in example 1.6 was converted to (RS)-{4-[Amino-(2-methoxy-ethoxyarbonylimino)-methyl]-phenylamino}-[5-ethoxy-2-fluoro-4-(2-hydroxy-ethoxy)-phenyl]-acetic acid ethyl ester by a reaction with 2-methoxyethyl chloroformate. MS: 522 ([M+H]$^+$).

1.16

In analogy to example 1.10, the (RS)-(4-carbamimidoyl-phenylamino)-[5-ethoxy-2-fluoro-4-(2-hydroxy-ethoxy)-phenyl]-acetic acid ethyl ester hydrochloride described in example 1.6 was converted to {4-[Amino-[1R-(2S-isopropyl-5R-methyl-cyclohexyl)oxycarbonylimino]-methyl]-phenylamino}-α(RS)-[5-ethoxy-2-fluoro-4-(2-hydroxy-ethoxy)-phenyl]-acetic acid ethyl ester by a reaction with (−)-(1R)-menthylchloroformate. MS: 602 ([M+H]$^+$).

1.17

In analogy to example 1.10, the (RS)-(4-carbamimidoyl-phenylamino)-[5-ethoxy-2-fluoro-4-(2-hydroxy-ethoxy)-phenyl]-acetic acid ethyl ester hydrochloride described in example 1.6 was converted to (RS)-[4-(Amino-prop-2-ynyloxycarbonylimino-methyl)-phenylamino]-[5-ethoxy-2-fluoro-4-(2-hydroxy-ethoxy)-phenyl]-acetic acid ethyl ester by a reaction with propargyl chloroformate. MS: 502 ([M+H]$^+$).

1.18

In analogy to example 1.10, the (RS)-(4-carbamimidoyl-phenylamino)-[5-ethoxy-2-fluoro-4-(2-hydroxy-ethoxy)-phenyl]-acetic acid ethyl ester hydrochloride described in example 1.6 was converted to (RS)-{4-[amino-(5-methyl-2-oxo-[1,3]dioxol-4-ylmethoxycarbonylimino)-methyl]-phenylamino}-[5-ethoxy-2-fluoro-4-(2-hydroxy-ethoxy)-phenyl]-acetic acid ethyl ester by a reaction with (5-methyl-2-oxo-1,3-dioxol-4-en-4-yl)methyl-p-nitrophenyl carbonate. MS: 576 ([M+H]$^+$).

1.19

The (RS)-[5-ethoxy-2-fluoro-4-(2-hydroxy-ethoxy)-phenyl]-[4-(N-hydroxycarbamimidoyl)-phenylamino]-acetic acid ethyl ester (218 mg) described in example 1.8 was dissolved in DMF (2 ml). Triethylamine (61 mg) and benzoyl chloride (77 mg) were added. After stirring for 1 h at room temperature, the mixture was poured into cold water and extracted with ethyl acetate. The product was purified by column chromatography (hexane/ethyl acetate) to give 230 mg of (R,S)-α-[[4-[[(benzoyloxy)amino]iminomethyl]phenyl]amino]-5-ethoxy-2-fluoro-4-(2-hydroxyethoxy)-benzeneacetic acid ethyl ester as a light yellow solid. MS: 540 ([M+H]$^+$).

1.20

The (RS)-[5-ethoxy-2-fluoro-4-(2-hydroxy-ethoxy)-phenyl]-[4-(N-hydroxycarbamimidoyl)-phenylamino]-acetic acid ethyl ester (300 mg) described in example 1.8 was dissolved in THF (3 ml). Ethyl isocyanate (54 mg) was added and the mixture was stirred for 2 h at room temperature. The mixture was concentrated and the residue was purified by column chromatography (hexane/EtOAc) to give 290 mg of (R,S)-5-ethoxy-α-[[4-[[[[(ethylamino)carbonyl]oxy]amino]iminomethyl]phenyl]amino]-2-fluoro-4-(2-hydroxyethoxy)-benzeneacetic acid ethyl ester as a colorless foam. MS: 507 ([M+H]$^+$).

1.21

In analogy to example 1.20, the (RS)-[5-ethoxy-2-fluoro-4-(2-hydroxy-ethoxy)-phenyl]-[4-(N-hydroxycarbamimidoyl)-phenylamino]-acetic acid ethyl ester described in example 1.8 was converted to (R,S)-5-ethoxy-2-fluoro-4-(2-hydroxyethoxy)-α-[[4-[imino [[[(phenylamino)carbonyl]oxy]amino]methyl]phenyl]amino]-benzeneacetic acid ethyl ester by a reaction with phenylisocyanate. MS: 555 ([M+H]$^+$).

1.22

In analogy to example 1.10, the (RS)-(4-carbamimidoyl-phenylamino)-[5-ethoxy-2-fluoro-4-(2-hydroxy-ethoxy)-phenyl]-acetic acid ethyl ester hydrochloride described in example 1.6 was converted to (RS)-{4-[amino-(4-fluoro-benzoylimino)-methyl]-phenylamino}-[5-ethoxy-2-fluoro-4-(2-hydroxy-ethoxy)-phenyl]-acetic acid ethyl ester by a reaction with 4-fluorobenzoyl chloride. MS: 542 ([M+Na]$^+$).

1.23

In analogy to example 1.10, the (RS)-(4-carbamimidoyl-phenylamino)-[5-ethoxy-2-fluoro-4-(2-hydroxy-ethoxy)-phenyl]-acetic acid ethyl ester hydrochloride described in example 1.6 was converted to (RS)-[4-(amino-benzoylimino-methyl)-phenylamino]-[5-ethoxy-2-fluoro-4-(2-hydroxy-ethoxy)-phenyl]-acetic acid ethyl ester by a reaction with benzoyl chloride. MS: 524 ([M+H]$^+$).

This compound was separated into the enantiomers by preparative HPLC on a chiral stationary phase (Chiralpak AD) using heptane/isopropanol/diethylamine (60:40:0.2) as a mobile phase to give (S)-[4-(amino-benzoylimino-methyl)-phenylamino]-[5-ethoxy-2-fluoro-4-(2-hydroxy-ethoxy)-phenyl]-acetic acid ethyl ester and (R)-[4-(amino-benzoylimino-methyl)-phenylamino]-[5-ethoxy-2-fluoro-4-(2-hydroxy-ethoxy)-phenyl]-acetic acid ethyl ester.

1.24

The (RS)-(4-carbamimidoyl-phenylamino)-[5-ethoxy-2-fluoro-4-(2-hydroxy-ethoxy)-phenyl]-acetic acid ethyl ester hydrochloride (456 mg) described in example 1.6 was dissolved in THF (3 ml). DMF (3 ml), triethylamine (106 mg) and phenylisocyanate (131 mg) were added and the mixture was stirred for 3 h at room temperature. The reaction mixture was concentrated and purified by column chromatography (hexane/ethyl acetate) to give 380 mg of (RS)-[4-(Amino-phenylcarbamoylimino-methyl)-phenylamino]-[5-ethoxy-2-fluoro-4-(2-hydroxy-ethoxy)-phenyl]-acetic acid ethyl ester as a colorless foam. MS: 539 ([M+H]$^+$).

1.25

In analogy to example 2.15, the (RS)-(4-cyano-phenylamino)-[5-ethoxy-2-fluoro-4-(2-hydroxy-ethoxy)-phenyl]-acetic acid ethyl ester described in example 1.5 was converted to (RS)-(4-cyano-phenylamino)-[5-ethoxy-2-fluoro-4-(2-hydroxy-ethoxy)-phenyl]-acetic acid by a reaction with LiOH. MS: 373 ([M–H]$^-$).

1.26

The (RS)-(4-cyano-phenylamino)-[5-ethoxy-2-fluoro-4-(2-hydroxy-ethoxy)-phenyl]-acetic acid (226 mg) described in example 1.25 was dissolved in DMF (2 ml). Potassium carbonate (167 mg), n-butyl iodide (556 mg) and tetrabutylammonium iodide (22 mg) were added and the mixture was stirred overnight at r.t. Water was added and the mixture was extracted with EtOAc. The org. phase was washed with water, dried, filtered and concentrated. The product was purified by chromatography (SiO$_2$, EtOAc/hexane) to give 146 mg of (RS)-(4-cyano-phenylamino)-[5-ethoxy-2-fluoro-4-(2-hydroxy-ethoxy)-phenyl]-acetic acid butyl ester as a colorless solid. MS: 453 ([M+Na]$^+$).

1.27

In analogy to example 2.5, the (RS)-(4-cyano-phenylamino)-[5-ethoxy-2-fluoro-4-(2-hydroxy-ethoxy)-phenyl]-acetic acid butyl ester described in example 1.26 was converted to (RS)-[5-Ethoxy-2-fluoro-4-(2-hydroxy-ethoxy)-phenyl]-[4-(N-hydroxycarbamimidoyl)-phenylamino]-acetic acid butyl ester by a reaction with triethylamine and hydroxylamine hydrochloride. MS: 464 ([M+H]$^+$).

This compound was separated into the enantiomers by preparative HPLC on a chiral stationary phase (Chiralpak AD) using heptane/ethanol/trifluoroacetic acid (80:20:0.2) as a mobile phase to give after neutralization (S)-[5-Ethoxy-2-fluoro-4-(2-hydroxy-ethoxy)-phenyl]-[4-(N-hydroxycarbamimidoyl)-phenylamino]-acetic acid butyl ester and (R)-[5-Ethoxy-2-fluoro-4-(2-hydroxy-ethoxy)-phenyl]-[4-(N-hydroxycarbamimidoyl)-phenylamino]-acetic acid butyl ester.

1.28

In analogy to example 1.26, the (RS)-(4-cyano-phenylamino)-[5-ethoxy-2-fluoro-4-(2-hydroxy-ethoxy)-phenyl]-acetic acid described in example 1.25 was converted to (RS)-(4-cyano-phenylamino)-[5-ethoxy-2-fluoro-4-(2-hydroxy-ethoxy)-phenyl]-acetic acid isopropyl ester by a reaction with isopropyl iodide. MS: 439 ([M+Na]$^+$).

1.29

In analogy to example 2.5, the (RS)-(4-cyano-phenylamino)-[5-ethoxy-2-fluoro-4-(2-hydroxy-ethoxy)-phenyl]-acetic acid isopropyl ester described in example 1.28 was converted to (RS)-[5-ethoxy-2-fluoro-4-(2-hydroxy-ethoxy)-phenyl]-[4-(N-hydroxycarbamimidoyl)-phenylamino]-acetic acid isopropyl ester by a reaction with triethylamine and hydroxylamine hydrochloride. MS: 450 ([M+H]$^+$).

This compound can be separated by methods known in the art, e.g. by preparative HPLC on a chiral stationary phase in analogy to example 1.27, to yield the corresponding R- and S-enatiomers.

1.30

In analogy to example 1.26, the (RS)-(4-cyano-phenylamino)-[5-ethoxy-2-fluoro-4-(2-hydroxy-ethoxy)-phenyl]-acetic acid described in example 1.25 was converted to (RS)-(4-cyano-phenylamino)-[5-ethoxy-2-fluoro-4-(2-hydroxy-ethoxy)-phenyl]-acetic acid benzyl ester by a reaction with benzyl bromide. MS: 487 ([M+Na]$^+$).

1.31

In analogy to example 2.5, the (RS)-(4-cyano-phenylamino)-[5-ethoxy-2-fluoro-4-(2-hydroxy-ethoxy)-phenyl]-acetic acid benzyl ester described in example 1.30 was converted to (RS)-[5-Ethoxy-2-fluoro-4-(2-hydroxy-ethoxy)-phenyl]-[4-(N-hydroxycarbamimidoyl)-phenylamino]-acetic acid benzyl ester by a reaction with triethylamine and hydroxylamine hydrochloride. MS: 498 ([M+H]$^+$).

This compound can be separated by methods known in the art, e.g. by preparative HPLC on a chiral stationary phase in analogy to example 1.27, to yield the corresponding R- and S-enatiomers.

1.32

In analogy to example 1.26, the (RS)-(4-cyano-phenylamino)-[5-ethoxy-2-fluoro-4-(2-hydroxy-ethoxy)-phenyl]-acetic acid described in example 1.25 was converted to (RS)-(4-cyano-phenylamino)-[5-ethoxy-2-fluoro-4-(2-hydroxy-ethoxy)-phenyl]-acetic acid isobutyl ester by a reaction with isobutyl iodide. MS: 430 ([M]$^+$).

1.33

In analogy to example 2.5, the (RS)-(4-cyano-phenylamino)-[5-ethoxy-2-fluoro-4-(2-hydroxy-ethoxy)-phenyl]-acetic acid isobutyl ester described in example 1.32 was converted to (RS)-[5-ethoxy-2-fluoro-4-(2-hydroxy-ethoxy)-phenyl]-[4-(N-hydroxycarbamimidoyl)-phenylamino]-acetic acid isobutyl ester by a reaction with triethylamine and hydroxylamine hydrochloride.

This compound can be separated by methods known in the art, e.g. by preparative HPLC on a chiral stationary phase in analogy to example 1.27, to yield the corresponding R- and S-enatiomers.

1.34

In analogy to example 1.10, (RS)-(4-carbamimidoyl-phenylamino)-[5-ethoxy-2-fluoro-4-(2-hydroxy-ethoxy)-phenyl]-acetic acid ethyl ester hydrochloride described in example 1.6 was converted to (RS)-{4-[amino-(2,4-difluoro-benzoylimino)-methyl]-phenylamino}-[5-ethoxy-2-fluoro-4-(2-hydroxy-ethoxy)-phenyl]-acetic acid ethyl ester by reaction with 2,4-difluorobenzoyl chloride. MS: 560 ([M+H]$^+$)

1.35

In analogy to example 1.10, (RS)-(4-carbamimidoyl-phenylamino)-[5-ethoxy-2-fluoro-4-(2-hydroxy-ethoxy)-phenyl]-acetic acid ethyl ester hydrochloride described in example 1.6 was converted to (RS)-{4-[amino-(3,5-dimethoxy-benzoylimino)-methyl]-phenylamino}-[5-ethoxy-2-fluoro-4-(2-hydroxy-ethoxy)-phenyl]-acetic acid ethyl ester by reaction with 3,5-dimethoxybenzoyl chloride. MS: 584 ([M+H]$^+$)

1.36

In analogy to example 1.10, (RS)-(4-carbamimidoyl-phenylamino)-[5-ethoxy-2-fluoro-4-(2-hydroxy-ethoxy)-phenyl]-acetic acid ethyl ester hydrochloride described in example 1.6 was converted to (RS)-{4-[amino-(3,4-dimethoxy-benzoylimino)-methyl]-phenylamino}-[5-ethoxy-2-fluoro-4-(2-hydroxy-ethoxy)-phenyl]-acetic acid ethyl ester by reaction with 3,4-dimethoxybenzoyl chloride. MS: 584 ([M+H]$^+$)

1.37

In analogy to example 1.10, (RS)-(4-carbamimidoyl-phenylamino)-[5-ethoxy-2-fluoro-4-(2-hydroxy-ethoxy)-phenyl]-acetic acid ethyl ester hydrochloride described in example 1.6 was converted to (RS)-{4-[amino-(3-fluoro-benzoylimino)-methyl]-phenylamino}-[5-ethoxy-2-fluoro-4-(2-hydroxy-ethoxy)-phenyl]-acetic acid ethyl ester by reaction with 3-fluorobenzoyl chloride. MS: 542 ([M+H]$^+$)

1.38

In analogy to example 1.10, (RS)-(4-carbamimidoyl-phenylamino)-[5-ethoxy-2-fluoro-4-(2-hydroxy-ethoxy)-phenyl]-acetic acid ethyl ester hydrochloride described in example 1.6 was converted to (RS)-{4-[Amino-(4-trifluoromethyl-benzoylimino)-methyl]-phenylamino}-[5-ethoxy-2-fluoro-4-(2-hydroxy-ethoxy)-phenyl]-acetic acid ethyl ester by reaction with 4-trifluoromethylbenzoyl chloride. MS: 592 ([M+H]$^+$)

1.39

In analogy to example 1.10, (RS)-(4-carbamimidoyl-phenylamino)-[5-ethoxy-2-fluoro-4-(2-hydroxy-ethoxy)-phenyl]-acetic acid ethyl ester hydrochloride described in example 1.6 was converted to (RS)-{4-[amino-(4-methyl-benzoylimino)-methyl]-phenylamino}-[5-ethoxy-2-fluoro-4-(2-hydroxy-ethoxy)-phenyl]-acetic acid ethyl ester by reaction with p-toluoylbenzoylchloride. MS: 538 ([M+H]$^+$)

Example 2

2.1

3,5-Bis-(tert-butyl-dimethyl-silanyloxy)-2-fluoro-benzaldehyde (19.51 g) was dissolved in DMF (100 ml). Potassium fluoride (11.79 g) and ethyl iodide (18.99 g) were added and the mixture was stirred for 3.5 h at room temperature. The mixture was poured into water and extracted with diethyl ether. The product was purified by column chromatography (hexane/ethyl acetate) to give 6.28 g of 3,5-diethoxy-2-fluoro-benzaldehyde as a colorless solid.

2.2

In analogy to example 1.5, the 3,5-diethoxy-2-fluoro-benzaldehyde described in example 2.1 was converted to (RS)-(4-cyano-phenylamino)-(3,5-diethoxy-2-fluoro-phenyl)-acetic acid ethyl ester by a reaction with 4-aminobenzonitrile and morpholinoethyl-isonitrile in the presence of boron trifluoride etherate. MS: 386 ([M]$^+$)

2.3

In analogy to example 1.6, the (RS)-(4-cyano-phenylamino)-(3,5-diethoxy-2-fluoro-phenyl)-acetic acid ethyl ester described in example 2.2 was converted to (RS)-(4-carbamimidoyl-phenylamino)-(3,5-diethoxy-2-fluoro-phenyl)-acetic acid ethyl ester hydrochloride by a reaction with HCl (gas) and EtOH followed by a reaction with ammonia. MS: 404 ([M+H]$^+$)

2.4

In analogy to example 1.7, the (RS)-(4-carbamimidoyl-phenylamino)-(3,5-diethoxy-2-fluoro-phenyl)-acetic acid ethyl ester hydrochloride described in example 2.3 was converted to (RS)-(4-carbamimidoyl-phenylamino)-(3,5-diethoxy-2-fluoro-phenyl)-acetic acid by hydrolysis with NaOH. MS: 376 ([M+H]$^+$).

This compound was separated into the enantiomers by preparative HPLC on a chiral stationary phase (Chiralpak AD) using heptane/ethanol/trifluoroacetic acid (75:25:0.2) as a mobile phase to give, after neutralization, (R)-(4-carbamimidoyl-phenylamino)-(3,5-diethoxy-2-fluoro-phenyl)-acetic acid and (S)-(4-carbamimidoyl-phenylamino)-(3,5-diethoxy-2-fluoro-phenyl)-acetic acid.

2.5

The (RS)-(4-cyano-phenylamino)-(3,5-diethoxy-2-fluoro-phenyl)-acetic acid ethyl ester (136 mg) described in example 2.2 was dissolved in ethanol. Triethylamine (712 mg) and hydroxylamine hydrochloride (245 mg) were added and the mixture was stirred for 18 h at room temperature. The mixture was concentrated; the residue was dissolved in CH$_2$Cl$_2$ and washed with water. The product was purified by column chromatography (CH$_2$Cl$_2$/MeOH) to give 87 mg of (RS)-(3,5-diethoxy-2-fluoro-phenyl)-[4-(N-hydroxycarbamimidoyl)-phenylamino]-acetic acid ethyl ester as a colorless foam. MS: 420 ([M+H]$^+$).

This compound was separated into the enantiomers by preparative HPLC on a chiral stationary phase (Chiralpak AD) using heptane/isopropanol/trifluoroacetic acid (80:20:0.2) as a mobile phase to give, after neutralization, (R)-(3,5-diethoxy-2-fluoro-phenyl)-[4-(N-hydroxycarbamimidoyl)-phenylamino]-acetic acid ethyl ester and (S)-(3,5-diethoxy-2-fluoro-phenyl)-[4-(N-hydroxycarbamimidoyl)-phenylamino]-acetic acid ethyl ester.

2.6

The (RS)-(3,5-diethoxy-2-fluoro-phenyl)-[4-(N-hydroxycarbamimidoyl)-phenylamino]-acetic acid ethyl ester (44 mg) described in example 2.5 was dissolved in THF (0.5 ml). IM NaOH (0.21 ml) was added and the mixture was stirred for 2 h at room temperature. The mixture was neutralized with 1 M HCl, concentrated and purified by column chromatography to give 23 mg of (RS)-(3,5-diethoxy-2-fluoro-phenyl)-[4-(N-hydroxycarbamimidoyl)-phenylamino]-acetic acid as a colorless solid. MS: 392 ([M+H]$^+$) This compound was separated into the enantiomers by preparative HPLC on a chiral stationary phase (Chiralpak AD) using heptane/isopropanol/trifluoroacetic acid (60:40:0.2) as a mobile phase to give, after neutralisation, (R)-(3,5-diethoxy-2-fluoro-phenyl)-[4-(N-hydroxycarbamimidoyl)-phenylamino]-acetic acid and (S)-(3,5-diethoxy-2-fluoro-phenyl)-[4-(N-hydroxycarbamimidoyl)-phenylamino]-acetic acid.

2.7

In analogy to example 1.10, the (RS)-(4-carbamimidoyl-phenylamino)-(3,5-diethoxy-2-fluoro-phenyl)-acetic acid ethyl ester hydrochloride described in example 2.3 was converted to (RS)-[4-(amino-ethoxycarbonylimino-methyl)-phenylamino]-(3,5-diethoxy-2-fluoro-phenyl)-acetic acid ethyl ester by a reaction with ethyl chloroformate. MS: 476 (M+H]$^+$)

2.8

In analogy to example 1.10, the (RS)-(4-carbamimidoyl-phenylamino)-(3,5-diethoxy-2-fluoro-phenyl)-acetic acid ethyl ester hydrochloride described in example 2.3 was converted to (RS)-{4-[amino-(4-fluoro-phenoxycarbonylimino)-methyl]-phenylamino}-(3,5-diethoxy-2-fluoro-phenyl)-acetic acid ethyl ester by a reaction with 4-fluorophenyl chloroformate. MS: 542 ([M+H]$^+$)

2.9

In analogy to example 1.10, the (RS)-(4-carbamimidoyl-phenylamino)-(3,5-diethoxy-2-fluoro-phenyl)-acetic acid ethyl ester hydrochloride described in example 2.3 was converted to (RS)-{4-[amino-(2,2,2-trichloro-ethoxycarbonylimino)-methyl]-phenylamino}-(3,5-diethoxy-2-fluoro-phenyl)-acetic acid ethyl ester by a reaction with 2,2,2-trichloroethyl chloroformate. MS: 580 ([M+H]$^+$)

2.10

In analogy to example 1.10, the (RS)-(4-carbamimidoyl-phenylamino)-(3,5-diethoxy-2-fluoro-phenyl)-acetic acid ethyl ester hydrochloride described in example 2.3 was converted to (RS)-{4-[amino-(5-methyl-2-oxo-[1,3]dioxol-4-ylmethoxycarbonylimino)-methyl]-phenylamino}-(3,5-diethoxy-2-fluoro-phenyl)-acetic acid ethyl ester by a reaction with (5-methyl-2-oxo-1,3-dioxol-4-en-4-yl)methyl-p-nitrophenyl carbonate. MS: 560 ([M+H]$^+$)

2.11

In analogy to example 1.10, the (RS)-(4-carbamimidoyl-phenylamino)-(3,5-diethoxy-2-fluoro-phenyl)-acetic acid ethyl ester hydrochloride described in example 2.3 was converted to (RS)-[4-(amino-methoxycarbonylimino-methyl)-phenylamino]-(3,5-diethoxy-2-fluoro-phenyl)-acetic acid ethyl ester by a reaction with methyl chloroformate. MS: 462 ([M+H]$^+$)

2.12

In analogy to example 1.10, the (RS)-(4-carbamimidoyl-phenylamino)-(3,5-diethoxy-2-fluoro-phenyl)-acetic acid ethyl ester hydrochloride described in example 2.3 was converted to (RS)-[4-(amino-phenoxycarbonylimino-methyl)-phenylamino]-(3,5-diethoxy-2-fluoro-phenyl)-acetic acid ethyl ester by a reaction with phenyl chloroformate. MS: 524 ([M+H]$^+$)

2.13

In analogy to example 1.10, the (RS)-(4-carbamimidoyl-phenylamino)-(3,5-diethoxy-2-fluoro-phenyl)-acetic acid ethyl ester hydrochloride described in example 2.3 was converted to (RS )-[4-(amino-isobutoxycarbonylimino-methyl)-phenylamino]-(3,5-diethoxy-2-fluoro-phenyl)-acetic acid ethyl ester by a reaction with isobutyl chloroformate. MS: 504 ([M+H]$^+$)

2.14

In analogy to example 1.10, the (RS)-(4-carbamimidoyl-phenylamino)-(3,5-diethoxy-2-fluoro-phenyl)-acetic acid ethyl ester hydrochloride described in example 2.3 was converted to (RS)-{4-[amino-(4-fluoro-benzoylimino)-methyl]-phenylamino}-(3,5-diethoxy-2-fluoro-phenyl)-acetic acid ethyl ester by a reaction with 4-fluorobenzoyl chloride. MS: 526 ([M+H]$^+$)

2.15

The (RS)-(4-cyano-phenylamino)-(3,5-diethoxy-2-fluoro-phenyl)-acetic acid ethyl ester (1.02 g) described in example 2.2 was dissolved in THF. 1 M LiOH (3.96 ml) was added and the mixture was stirred for 2 h at room temperature. 1 M HCl (4 ml) was added. The product was isolated by extraction with ethyl acetate to give 970 mg of (RS)-(4-cyano-phenylamino)-(3,5-diethoxy-2-fluoro-phenyl)-acetic acid which was used for the next step without further purification. MS: 357 ([M–H]$^-$)

2.16

The (RS)-(4-cyano-phenylamino)-(3,5-diethoxy-2-fluoro-phenyl)-acetic acid (220 mg) described in example 2.15 was dissolved in THF (3.3 ml). n-Butanol (64 mg), triphenylphosphine (179 mg) and diethylazo dicarboxylate (122 mg) were added and the mixture was stirred for 3 h at room temperature. The mixture was concentrated and the product was purified by column chromatography to give 109 mg of (RS)-(4-cyano-phenylamino)-(3,5-diethoxy-2-fluoro-phenyl)-acetic acid butyl ester as an off-white solid. MS: 414 ([M+H]$^+$)

2.17

In analogy to example 2.5, the (RS)-(4-cyano-phenylamino)-(3,5-diethoxy-2-fluoro-phenyl)-acetic acid butyl ester described in example 2.16 was converted to (RS)-(3,5-diethoxy-2-fluoro-phenyl)-[4-(N-hydroxycarbamimidoyl)-phenylamino ]-acetic acid butyl ester by a reaction with triethylamine and hydroxylamine hydrochloride. MS: 448 ([M+H]$^+$)

2.18

In analogy to example 2.16, the (RS)-(4-cyano-phenylamino)-(3,5-diethoxy-2-fluoro-phenyl)-acetic acid described in example 2.15 was converted to (RS)-(4-cyano-phenylamino)-(3,5-diethoxy-2-fluoro-phenyl)-acetic acid isopropyl ester by a reaction with isopropanol, triphenylphosphine and diethylazo dicarboxylate. MS: 400 ([M]$^+$)

2.19

In analogy to example 2.5, the (RS)-(4-cyano-phenylamino)-(3,5-diethoxy-2-fluoro-phenyl)-acetic acid isopropyl ester described in example 2.18 was converted to (RS)-(3,5-diethoxy-2-fluoro-phenyl)-[4-(N-hydroxycarbamimidoyl)-phenylamino]-acetic acid isopropyl ester by a reaction with triethylamine and hydroxylamine hydrochloride. MS: 434 ([M]$^+$)

Example 3

3.1

A solution of 53.0 g 5-(tert-butyl-dimethyl-silanyloxy)-2-fluoro-phenol (M. Kawase, A. K. Sinhababu, R. T. Borchardt, Chem. Pharm. Bull. (1990),38, 2939) in 120 ml DMF was cooled to 0° C. Within 15 min 61.6 ml tert-butyldiphenylsilyl chloride were added. Then 16.4 g imidazole were added portionwise. The suspension was stirred overnight, then quenched with 150 ml H$_2$O at 0° C. The crude product was isolated by extraction with hexanes and purified by chromatography on silica gel (hexanes) to yield 88.9 g of 4-(tert-butyl-dimethyl-silanyloxy)-2-(tert-butyl-diphenyl-silanyloxy)-fluorobenzene as colorless liquid.

3.2

A solution of 55.0 g of 4-(tert-butyl-dimethyl-silanyloxy)-2-(tert-butyl-diphenyl-silanyloxy)-fluorobenzene described in example 3.1 in 120 ml THF was cooled to −78° C. Within 30 min 97 ml of an 1.3 M solution of sec-butyllithium in cyclohexane was added dropwise. After stirring at −78° C. for an hour, 9.7 DMF in 18.3 ml THF was added within 20 min. The mixture was stirred at −78° C. for 1 hr, then warmed to r.t. within 90 min and quenched with 300 ml ice-cold water. The product was isolated by extraction with Et$_2$O to yield 60.6 g 5-(tert-butyl-dimethyl-silanyloxy)-3-(tert-butyl-diphenyl-silanyloxy)-2-fluoro-benzaldehyde as yellow liquid.

3.3

A solution of 35.0 g 5-(tert-butyl-dimethyl-silanyloxy)-3-(tert-butyl-diphenyl-silanyloxy)-2-fluoro-benzaldehyde described in example 3.2 and 8.13 g 4-aminobenzonitrile in 250 ml EtOH was stirred for 1 hr at r.t. Then 13.43 g toluene-4-sulfonylmethyl isocyanide were added. The solution was cooled to 0° C. Subsequently, 25.9 ml of boron trifluoride diethyl etherate were added in a manner such that the temperature did not exceed 5° C. The mixture was stirred for 15 min at 0° C. and for 2 hrs at r.t. and subsequently treated with 25 ml H$_2$O. The solution was stirred at 50° C. over night. The crude product was isolated by extraction with EtOAc and purified by chromatography on silica gel (cyclohexane/EtOAc) to yield 22.38 g (RS)-[3-(tert-butyl-diphenyl-silanyloxy)-2-fluoro-5-hydroxy-phenyl]-(4-cyano-phenylamino)-acetic acid ethyl ester as amorphous, slightly yellow solid.

3.4

To a solution of 49 g (RS)-[3-(tert-butyl-diphenyl-silanyloxy)-2-fluoro-5-hydroxy-phenyl]-(4-cyano-phenylamino)-acetic acid ethyl ester described in example 3.3 in 900 ml THF 24.86 g triphenylphosphine, 5.53 ml EtOH and 21.82 g di-tert-butyl azodicarboxylate were added sequentially. The solution was stirred for 4 hrs at room temperature and then evaporated. The crude product was purified by chromatography on silica gel (cyclohexane/EtOAc) to yield 27.6 g (RS)-[3-(tert-butyl-diphenyl-silanyloxy)-5-ethoxy-2-fluoro-phenyl]-(4-cyano-phenylamino)-acetic acid ethyl ester as slightly yellow, amorphous solid.

3.5

A solution of 27.6 g (RS)-[3-(tert-butyl-diphenyl-silanyloxy)-5-ethoxy-2-fluoro-phenyl]-(4-cyano-phenylamino)-acetic acid ethyl ester described in example 3.4 in 470 ml THF was cooled to 0° C. and treated with 50.9 ml 1M tetrabutylammonium fluoride solution in THF. The reaction mixture was stirred at 0° C. for 4 hrs. The crude product was isolated by extraction with EtOAc and purified by chromatography on silica gel (cyclohexane/EtOAc) to yield 12.89 g (RS)-(4-cyano-phenylamino)-(5-ethoxy-2-fluoro-3-hydroxy-phenyl)-acetic acid ethyl ester as a yellow semisolid.

3.6

To a solution of 7.38 g (RS)-(4-cyano-phenylamino)-(5-ethoxy-2-fluoro-3-hydroxy-phenyl)-acetic acid ethyl ester described in example 3.5 in 220 ml THF were added 1.68 ml (S)-(+)-3-hydroxy-tetrahydrofurane and 6.48 g triphenylphosphine. The mixture was cooled to 0° C. Subsequently, 3.84 ml of diethyl azodicarboxylate were added. The solution was stirred for 3 hrs at room temperature, then evaporated. The crude product was purified by chromatography on silica gel (cyclohexane/EtOAc) to give 6.53 g of (RS)-(4-cyano-phenylamino)-[5-ethoxy-2-fluoro-3-[(R)-tetrahydro-furan-3-yloxy]-phenyl]-acetic acid ethyl ester as an off-white solid.

3.7

To a mixture of 8.85 g (RS)-(4-cyano-phenylamino)-[5-ethoxy-2-fluoro-3-[(R)-tetrahydro-furan-3-yloxy]-phenyl]-acetic acid ethyl ester described in example 3.6 in 515 ml EtOH were added 20.21 g hydroxylamine hydrochloride and 81.1 ml triethylamine. The solution was stirred over night at 50° C., then evaporated. The crude product was isolated by extraction with EtOAc, then purified by chromatography on silica gel (CH$_2$Cl$_2$/MeOH) to yield 7.64 g (RS)-[5-ethoxy-2-fluoro-3-[(R)-tetrahydro-furan-3-yloxy]-phenyl]-[4-(N-hydroxycarbamimidoyl)-phenylamino]-acetic acid ethyl ester as a light brown amorphous solid.

This isomeric mixture was separated into the diastereomers by preparative HPLC on a chiral stationary phase (Chiralpak AD) using heptane/isopropanol/trifluoroacetic acid (70:30:0.2) as a mobile phase to give, after neutralization, (R)-[5-ethoxy-2-fluoro-3-[(R)-tetrahydro-furan-3-yloxy]-phenyl]-[4-(N-hydroxycarbamimidoyl)-phenylamino]-acetic acid ethyl ester and (S)-[5-ethoxy-2-fluoro-3-[(R)-tetrahydro-furan-3-yloxy)-phenyl]-[4-(N-hydroxycarbamimidoyl)-phenylamino]-acetic acid ethyl ester as amorphous solids.

3.8

A solution of 3.85 g (RS)-(4-cyano-phenylamino)-[5-ethoxy-2-fluoro-3-[(R)-tetrahydro-furan-3-yloxy]-phenyl]-acetic acid ethyl ester described in example 3.6 were dissolved in 80 ml CHCl$_3$/EtOH 3:1 and cooled to −10° C. Then, a stream of dry HCl gas was passed through the mixture during 1 hr. The reaction was kept at −4° C.

overnight, then evaporated. The residue was taken up in 35 ml 2M NH₃ in EtOH and stirred at 60° C. for 2 hrs. The reaction mixture was evaporated. The crude product was purified by chromatography on silica gel (CH₂Cl₂MeOH) to give 4.04 g of (RS)-(4-carbamimidoyl-phenylamino)-[5-ethoxy-2-fluoro-3-[(R)-tetrahydro-furan-3-yloxy]-phenyl]-acetic acid ethyl ester hydrochloride as an off-white solid.

3.9

A suspension of 170 mg (RS)-(4-carbamimidoyl-phenylamino)-[5-ethoxy-2-fluoro-3-[(R)-tetrahydro-furan-3-yloxy]-phenyl]-acetic acid ethyl ester hydrochloride described in example 3.8 in 5 ml THF was cooled to 0° C. and treated with 1.8 ml 1N LiOH solution. The mixture was stirred for 2 hrs at 0° C., then neutralized with 1N HCl. The precipitate was filtered off and washed with H₂O and Et₂O to yield 129 mg of (RS)-(4-carbamimidoyl-phenylamino)-[5-ethoxy-2-fluoro-3-[(R)-tetrahydro-furan-3-yloxy]-phenyl]-acetic acid as an off-white solid. This isomeric mixture was separated into the diastereomers by preparative HPLC on a chiral stationary phase (Chiralpak AD) using heptane/isopropanol/trifluoroacetic acid (75:25:0.2) as a mobile phase to give, after neutralization, (R)-(4-carbamimidoyl-phenylamino)-[5-ethoxy-2-fluoro-3-[(R)-tetrahydro-furan-3-yloxy]-phenyl]-acetic acid and (S)-(4-carbamimidoyl-phenylamino)-[5-ethoxy-2-fluoro-3-(R)-tetrahydro-furan-3-yloxy]-phenyl]-acetic acid as off-white solids.

3.10

In analogie to example 3.6 (RS)-(4-cyano-phenylamino)-(5-ethoxy-2-fluoro-3-hydroxy-phenyl)-acetic acid ethyl ester was reacted with (R)-(−)-3-hydroxytetrahydrofurane to (R)- and (S)-(4-cyano-phenylamino)-[5-ethoxy-2-fluoro-3-[(S)-tetrahydro-furan-3-yloxy]-phenyl]-acetic acid ethyl ester. In analogie to example 3.8 and 3.9 this material was converted via (RS)-(4-carbamimidoyl-phenylamino)-[5-ethoxy-2-fluoro-3-[(S)-tetrahydro-furan-3-yloxy]phenyl]-acetic acid ethyl ester hydrochloride to (RS)-(4-carbamimidoyl-phenylamino)-[5-ethoxy-2-fluoro-3-[(S)-tetrahydro-furan-3-yloxy]-phenyl]-acetic acid.

This isomeric mixture was separated into the diastereomers by preparative HPLC on a chiral stationary phase (Chiralpak AD) using heptane/isopropanol/trifluoroacetic acid (80:20:0.2) as a mobile phase to give, after neutralization, (R)-(4-carbamimidoyl-phenylamino)-[5-ethoxy-2-fluoro-3-[(S)-tetrahydro-furan-3-yloxy]-phenyl]-acetic acid and (S)-(4-carbamimidoyl-phenylamino)-[5-ethoxy-2-fluoro-3-[(S)-tetrahydro-furan-3-yloxy]-phenyl]-acetic acid as off-white solids.

3.11

In analogy to example 3.7 the (RS)-(4-cyano-phenylamino)-[5-ethoxy-2-fluoro-3-[(S)-tetrahydro-furan-3-yloxy]-phenyl]-acetic acid ethyl ester described in example 3.10 was converted to (RS)-[5-ethoxy-2-fluoro-3-[(S)-tetrahydro-furan-3-yloxy]-phenyl]-[4-(N-hydroxycarbamimidoyl)-phenylamino]-acetic acid ethyl ester.

| Example A: Pharmaceutical Composition I | |
|---|---|
| | Per tablet |
| Active substance | 200 mg |
| Microcrystalline cellulose | 155 mg |

| Example A: Pharmaceutical Composition I (continued) | |
|---|---|
| | Per tablet |
| Maize starch | 25 mg |
| Talc | 25 mg |
| Hydroxypropylmethylcellulose | 20 mg |
| | 425 mg |

| Example B: Pharmaceutical Composition II | |
|---|---|
| | pro Capsule |
| Active substance | 100.0 mg |
| Maize starch | 20.0 mg |
| Lactose | 95.0 mg |
| Talc | 4.5 mg |
| Magnesium stearate | 0.5 mg |
| | 220.0 mg |

The subject invention has been described in terms of its preferred embodiments. Upon reading the present specification, various alternative embodiments will become obvious to the skilled artisan. These variations are to be considered within the scope and spirit of the subject invention, which is only to be limited by the claims that follow and there equivalents.

What is claimed is:

1. A compound of the formula:

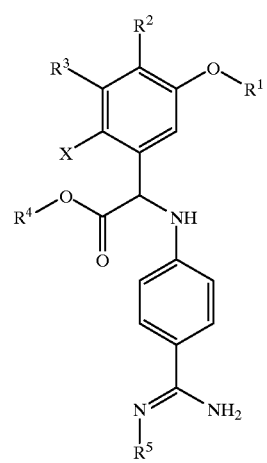

I wherein
R¹ is alkyl;
R² is hydrogen, hydroxyalkoxy, alkoxycarbonyloxyalkoxy, or halogenalkoxycarbonyloxyalkoxy;
R³ is hydrogen, alkoxy, or heterocycloalkyloxy;
R⁴ is hydrogen or the residue of an ester group which is cleavable under physiological conditions;
R⁵ is hydrogen, hydroxy, alkoxycarbonyl, halogenalkoxycarbonyl, aryloxycarbonyl, arylalkoxycarbonyl, alkoxyalkoxycarbonyl, cycloalkyloxycarbonyl, alkynyloxycarbonyl, 5-methyl-2-oxo-[1,3] dioxol-4-ylmethoxycarbonyl, arylcarbonyloxy, alkylaminocarbonyloxy, arylaminocarbonyloxy, alkylcarbonyl, arylcarbonyl, heteroarylcarbonyl, or arylaminocarbonyl; and X is F, Cl, or Br;

or a hydrate or solvates thereof, or a physiologically acceptable salt thereof or a physiologically acceptable ester thereof, with the provisio that the compound of formula I is not selected from the group consisting of:

(RS)-(4-carbamimidoyl-phenylamino)-(3,5-diethoxy-2-fluoro-phenyl)-acetic acid ethyl ester, (RS)-(4-carbamimidoyl-phenylamino)-(3,5-diethoxy-2-fluoro-phenyl)-acetic acid, (RS)-(4-carbamimidoyl-phenylamino)-(2-fluoro-3,5-dimethoxy-phenyl)-acetic acid, and (RS)-(4-carbamimidoyl-phenylamino)-(2-fluoro-3,5-dimethoxy-phenyl)-acetic acid ethyl ester.

2. The compound according to claim 1, wherein $R^1$ is ethyl.

3. The compound according to claim 1, wherein only one of $R^2$ and $R^3$ is hydrogen.

4. The compound according to claim 1, wherein $R^2$ is hydrogen.

5. The compound according to claim 1, wherein $R^2$ is hydroxyalkoxy.

6. The compound according to claim 5, wherein $R^2$ is 2-hydroxy-ethoxy.

7. The compound according to claim 1, wherein $R^2$ is alkoxycarbonyloxyalkoxy or halogenalkoxycarbonyloxyalkoxy.

8. The compound according to claim 1, wherein $R^2$ is alkoxycarbonyloxyalkoxy.

9. The compound according to claim 1, wherein $R^2$ is halogenalkoxycarbonyloxyalkoxy.

10. The compound according to claim 9, wherein $R^2$ is 2-(2,2,2-trichloro-ethoxycarbonyloxy)-ethoxy.

11. The compound according to claim 1, wherein $R^3$ is hydrogen.

12. The compound according to claim 1, wherein $R^3$ is alkoxy.

13. The compound according to claim 12, wherein $R^3$ is ethoxy.

14. The compound according to claim 1, wherein $R^3$ is heterocycloalkyloxy.

15. The compound according to claim 14, wherein $R^3$ is tetrahydrofuran-3-yloxy.

16. The compound according to claim 1, wherein $R^4$ is hydrogen, alkyl, or aryl-alkyl.

17. The compound according to claim 16, wherein $R^4$ is hydrogen.

18. The compound according to claim 16, wherein $R^4$ is alkyl.

19. The compound according to claim 18, wherein $R^4$ is ethyl, iso-propyl, butyl, or iso-butyl.

20. The compound according to claim 19, wherein $R^4$ is ethyl.

21. The compound according to claim 16, wherein $R^4$ is aryl-alkyl.

22. The compound according to claim 21, wherein $R^4$ is benzyl.

23. The compound according to claim 1, wherein $R^5$ is hydrogen, hydroxy, ethoxycarbonyl, 2,2,2-trichloro-ethoxycarbonyl, methoxycarbonyl, 4-fluoro-phenyloxycarbonyl, benzyloxycarbonyl, 2-methoxy-ethoxycarbonyl, 2-isopropyl-5-methyl-cyclohexyloxycarbonyl, prop-2-ynyloxycarbonyl, 5-methyl-2-oxo-[1,3]dioxol-4-ylmethoxycarbonyl, benzoyloxy, ethylaminocarbonyloxy, phenylaminocarbonyloxy, benzoyl, 3-fluoro-benzoyl, 4-fluoro-benzoyl, 2,4-difluoro-benzoyl, 3,4-dimethoxy-benzoyl, 3,5-dimethoxy-benzoyl, 4-methyl-benzoyl, 4-trifluoromethyl-benzoyl, phenylaminocarbonyl, or isobutoxycarbonyl.

24. The compound according to claim 23, wherein $R^5$ is hydrogen.

25. The compound according to claim 24, wherein $R^5$ is hydroxy.

26. The compound according to claim 1, wherein $R^5$ is alkoxycarbonyl, halogenalkoxycarbonyl, aryloxycarbonyl, arylalkoxycarbonyl, alkoxyalkoxycarbonyl, cycloalkyloxycarbonyl, alkynyloxycarbonyl, 5-methyl-2-oxo-[1,3]dioxol-4-ylmethoxycarbonyl, arylcarbonyloxy, alkylaminocarbonyloxy, arylaminocarbonyloxy, alkylcarbonyl, arylcarbonyl, heteroarylcarbonyl, or arylaminocarbonyl.

27. The compound according to claim 26, wherein $R^5$ is alkoxycarbonyl, halogenalkoxycarbonyl, alkoxyalkoxycarbonyl, cycloalkyloxycarbonyl, alkynyloxycarbonyl, alkylaminocarbonyloxy, or alkylcarbonyl.

28. The compound according to claim 27, $R^5$ is 2,2,2-trichloro-ethoxycarbonyl.

29. The compound according to claim 26, wherein $R^5$ is alkylaminocarbonyloxy.

30. The compound according to claim 26, wherein $R^5$ is aryloxycarbonyl, arylalkoxycarbonyl, arylaminocarbonyloxy, arylcarbonyl, or arylaminocarbonyl.

31. The compound according to claim 30, wherein $R^5$ is benzoyl.

32. The compound according to claim 26, wherein $R^5$ is alkylaminocarbonyloxy.

33. The compound according to claim 26, wherein $R^5$ is arylcarbonyloxy or arylaminocarbonyloxy.

34. The compound according to claim 26, wherein $R^5$ is 5-methyl-2-oxo-[1,3]dioxol-4-ylmethoxycarbonyl.

35. The compound of claim 26, wherein $R^5$ is heteroarylcarbonyl.

36. The compound according to claim 1, wherein X is F.

37. The compound according to claim 1, wherein the compound is of the formula:

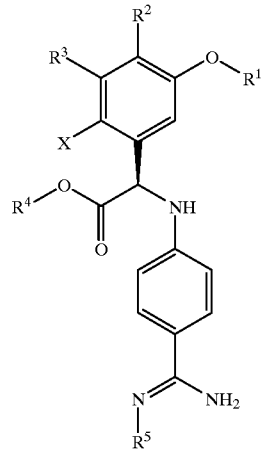

Ia wherein $R^1$, $R^2$, $R^3$, $R^4$, $R^5$, and X are as in claim 1.

38. The compound according to claim 1 which is (RS)-(4-carbamimidoyl-phenylamino)-[5-ethoxy-2-fluoro-4-(2-hydroxy-ethoxy)-phenyl]-acetic acid ethyl ester hydrochoride.

39. The compound according to claim 1 which is (RS)-(4-carbamimidoyl-phenylamino)-[5-ethoxy-2-fluoro-4-(2-hydroxy-ethoxy)-phenyl]-acetic acid.

40. The compound according to claim 1 which is (S)-(4-carbamimidoyl-phenylamino)-[5-ethoxy-2-fluoro-4-(2-hydroxy-ethoxy)-phenyl]-acetic acid.

41. The compound according to claim 1 which is (R)-(4-carbamimidoyl-phenylamino)-[5-ethoxy-2-fluoro-4-(2-hydroxy-ethoxy)-phenyl]-acetic acid.

42. The compound according to claim 1 which is (RS)-[5-ethoxy-2-fluoro-4-(2-hydroxy-ethoxy)-phenyl]-[4-(N-hydroxycarbamimidoyl)-phenylamino]-acetic acid ethyl ester.

43. The compound according to claim 1 which is (S)-[5-ethoxy-2-fluoro-4-(2-hydroxy-ethoxy)-phenyl]-[4-(N-hydroxycarbamimidoyl)-phenylamino]-acetic acid ethyl ester.

44. The compound according to claim 1 which is (R)-[5-ethoxy-2-fluoro-4-(2-hydroxy-ethoxy)-phenyl]-[4-(N-hydroxycarbamimidoyl)-phenylamino]-acetic acid ethyl ester.

45. The compound according to claim 1 which is (RS)-[5-ethoxy-2-fluoro-4-(2-hydroxy-ethoxy)-phenyl]-[4-(N-hydroxycarbamimidoyl)-phenylamino]-acetic acid sodiumchloride.

46. The compound according to claim 1 which is (RS)-[4-(amino-ethoxycarbonylimino-methyl)-phenylamino]-[5-ethoxy-2-fluoro-4-(2-hydroxy-ethoxy)-phenyl]-acetic acid ethyl ester.

47. The compound according to claim 1 which is (RS)-{4-[amino-(2,2,2-trichloro-ethoxycarbonylimino)-methyl]-phenylamino}-{5-ethoxy-2-fluoro-4-[2-(2,2,2-trichloro-ethoxycarbonyloxy)-ethoxy]-phenyl}-acetic acid ethyl ester.

48. The compound according to claim 1 which is (RS)-{4-[amino-(2,2,2-trichloro-ethoxycarbonylimino)-methyl]-phenylamino}-[5-ethoxy-2-fluoro-4-(2-hydroxy-ethoxy)-phenyl]-acetic acid ethyl ester.

49. The compound according to claim 1 which is (S)-{4-[amino-(2,2,2-trichloro-ethoxycarbonylimino)-methyl]-phenylamino}-[5-ethoxy-2-fluoro-4-(2-hydroxy-ethoxy)-phenyl]-acetic acid ethyl ester.

50. The compound according to claim 1 which is (R)-{4-[amino-(2,2,2-trichloro-ethoxycarbonylimino)-methyl]-phenylamino}-[5-ethoxy-2-fluoro-4-(2-hydroxy-ethoxy)-phenyl]-acetic acid ethyl ester.

51. The compound according to claim 1 which is (RS)-[4-(amino-methoxycarbonylimino-methyl)-phenylamino]-[5-ethoxy-2-fluoro-4-(2-hydroxy-ethoxy)-phenyl]-acetic acid ethyl ester.

52. The compound according to claim 1 which is (RS)-{4-[amino-(4-fluoro-phenoxycarbonylimino)-methyl]-phenylamino}-[5-ethoxy-2-fluoro-4-(2-hydroxy-ethoxy)-phenyl]-acetic acid ethyl ester.

53. The compound according to claim 1 which is (RS)-[4-(amino-benzyloxycarbonylimino-methyl)-phenylamino]-[5-ethoxy-2-fluoro-4-(2-hydroxy-ethoxy)-phenyl]-acetic acid ethyl ester.

54. The compound according to claim 1 which is (RS)-{4-[amino-(2-methoxy-ethoxycarbonylimino)-methyl]-phenylamino}-[5-ethoxy-2-fluoro-4-(2-hydroxy-ethoxy)-phenyl]-acetic acid ethyl ester.

55. The compound according to claim 1 which is {4-[amino-[1R-(2S-isopropyl-5R-methyl-cyclohexyl)oxycarbonylimino]-methyl]-phenylamino}-α(RS)-[5-ethoxy-2-fluoro-4-(2-hydroxy-ethoxy)-phenyl]-acetic acid ethyl ester.

56. The compound according to claim 1 which is (RS)-[4-(amino-prop-2-ynyloxycarbonylimino-methyl)-phenylamino]-[5-ethoxy-2-fluoro-4-(2-hydroxy-ethoxy)-phenyl]-acetic acid ethyl ester.

57. The compound according to claim 1 which is (RS)-{4-[amino-(5-methyl-2-oxo-[1,3]dioxol-4-ylmethoxycarbonylimino)-methyl]-phenylamino}-[5-ethoxy-2-fluoro-4-(2-hydroxy-ethoxy)-phenyl]-acetic acid ethyl ester.

58. The compound according to claim 1 which is (R,S)-α-[[4-[[(Benzoyloxy)amino]iminomethyl]phenyl]amino]-5-ethoxy-2-fluoro-4-(2-hydroxyethoxy)-benzeneacetic acid ethyl ester.

59. The compound according to claim 1 which is (R,S)-5-ethoxy-α-[[4-[[[[(ethylamino)carbonyl]oxy]amino]iminomethyl]phenyl]amino]-2-fluoro-4-(2-hydroxyethoxy)-benzeneacetic acid ethyl ester.

60. The compound according to claim 1 which is (R,S)-5-ethoxy-2-fluoro-4-(2-hydroxyethoxy)-α-[[4-[imino[[[(phenylamino)carbonyl]oxy]amino]methyl]phenyl]amino]-benzeneacetic acid ethyl ester.

61. The compound according to claim 1 which is (RS)-{4-[amino-(4-fluoro-benzoylimino)-methyl]-phenylamino}-[5-ethoxy-2-fluoro-4-(2-hydroxy-ethoxy)-phenyl]-acetic acid ethyl ester.

62. The compound according to claim 1 which is (RS)-[4-(amino-benzoylimino-methyl)-phenylamino]-[5-ethoxy-2-fluoro-4-(2-hydroxy-ethoxy)-phenyl]-acetic acid ethyl ester.

63. The compound according to claim 1 which is (S)-[4-(amino-benzoylimino-methyl)-phenylamino]-[5-ethoxy-2-fluoro-4-(2-hydroxy-ethoxy)-phenyl]-acetic acid ethyl ester.

64. The compound according to claim 1 which is (R)-[4-(amino-benzoylimino-methyl)-phenylamino]-[5-ethoxy-2-fluoro-4-(2-hydroxy-ethoxy)-phenyl]-acetic acid ethyl ester.

65. The compound according to claim 1 which is (RS)-[4-(amino-phenylcarbamoylimino-methyl)-phenylamino]-[5-ethoxy-2-fluoro-4-(2-hydroxy-ethoxy)-phenyl]-acetic acid ethyl ester.

66. The compound according to claim 1 which is (RS)-[5-ethoxy-2-fluoro-4-(2-hydroxy-ethoxy)-phenyl]-[4-(N-hydroxycarbamimidoyl)-phenylamino]-acetic acid butyl ester.

67. The compound according to claim 1 which is (S)-[5-ethoxy-2-fluoro-4-(2-hydroxy-ethoxy)-phenyl]-[4-(N-hydroxycarbamimidoyl)-phenylamino]-acetic acid butyl ester.

68. The compound according to claim 1 which is (R)-[5-ethoxy-2-fluoro-4-(2-hydroxy-ethoxy)-phenyl]-[4-(N-hydroxycarbamimidoyl)-phenylamino]-acetic acid butyl ester.

69. The compound according to claim 1 which is (RS)-[5-ethoxy-2-fluoro-4-(2-hydroxy-ethoxy)-phenyl]-[4-(N-hydroxycarbamimidoyl)-phenylamino]-acetic acid isopropyl ester.

70. The compound according to claim 1 which is (S)-[5-ethoxy-2-fluoro-4-(2-hydroxy-ethoxy)-phenyl]-[4-(N-hydroxycarbamimidoyl)-phenylamino]-acetic acid isopropyl ester.

71. The compound according to claim 1 which is (R)-[5-ethoxy-2-fluoro-4-(2-hydroxy-ethoxy)-phenyl]-[4-(N-hydroxycarbamimidoyl)-phenylamino]-acetic acid isopropyl ester.

72. The compound according to claim 1 which is (RS)-[5-ethoxy-2-fluoro-4-(2-hydroxy-ethoxy)-phenyl]-[4-(N-hydroxycarbamimidoyl)-phenylamino]-acetic acid benzyl ester.

73. The compound according to claim 1 which is (S)-[5-ethoxy-2-fluoro-4-(2-hydroxy-ethoxy)-phenyl]-[4-(N-hydroxycarbamimidoyl)-phenylamino]-acetic acid benzyl ester.

74. The compound according to claim 1 which is (R)-[5-ethoxy-2-fluoro-4-(2-hydroxy-ethoxy)-phenyl]-[4-(N-hydroxycarbamimidoyl)-phenylamino]-acetic acid benzyl ester.

75. The compound according to claim 1 which is (RS)-[5-ethoxy-2-fluoro-4-(2-hydroxy-ethoxy)-phenyl]-[4-(N-hydroxycarbamimidoyl)-phenylamino]-acetic acid isobutyl ester.

76. The compound according to claim 1 which is (S)-[5-ethoxy-2-fluoro-4-(2-hydroxy-ethoxy)-phenyl]-[4-(N-hydroxycarbamimidoyl)-phenylamino]-acetic acid isobutyl ester.

77. The compound according to claim 1 which is (R)-[5-ethoxy-2-fluoro-4-(2-hydroxy-ethoxy)-phenyl]-[4-(N-hydroxycarbamimidoyl)-phenylamino]-acetic acid isobutyl ester.

78. The compound according to claim 1 which is (RS)-{4-[amino-(2,4-difluoro-benzoylimino)-methyl]-phenylamino}-[5-ethoxy-2-fluoro-4-(2-hydroxy-ethoxy)-phenyl]-acetic acid ethyl ester.

79. The compound according to claim 1 which is (RS)-{4-[amino-(3,5-dimethoxy-benzoylimino)-methyl]-phenylamino}-[5-ethoxy-2-fluoro-4-(2-hydroxy-ethoxy)-phenyl]-acetic acid ethyl ester.

80. The compound according to claim 1 which is (RS)-{4-[amino-(3,4-dimethoxy-benzoylimino)-methyl]-phenylamino}-[5-ethoxy-2-fluoro-4-(2-hydroxy-ethoxy)-phenyl]-acetic acid ethyl ester.

81. The compound according to claim 1 which is (RS)-{4-[amino-(3-fluoro-benzoylimino)-methyl]-phenylamino}-[5-ethoxy-2-fluoro-4-(2-hydroxy-ethoxy)-phenyl]-acetic acid ethyl ester.

82. The compound according to claim 1 which is (RS)-{4-[amino-(4-trifluoromethyl-benzoylimino)-methyl]-phenylamino}-[5-ethoxy-2-fluoro-4-(2-hydroxy-ethoxy)-phenyl]-acetic acid ethyl ester.

83. The compound according to claim 1 which is (RS)-{4-[amino-(4-methyl-benzoylimino)-methyl]-phenylamino}-[5-ethoxy-2-fluoro-4-(2-hydroxy-ethoxy)-phenyl]-acetic acid ethyl ester.

84. The compound according to claim 1 which is (R)-(4-carbamimidoyl-phenylamino)-(3,5-diethoxy-2-fluoro-phenyl)-acetic acid.

85. The compound according to claim 1 which is (S)-(4-carbamimidoyl-phenylamino)-(3,5-diethoxy-2-fluoro-phenyl)-acetic acid.

86. The compound according to claim 1 which is (RS)-(3,5-diethoxy-2-fluoro-phenyl)-[4-(N-hydroxycarbamimidoyl)-phenylamino]-acetic acid ethyl ester.

87. The compound according to claim 1 which is (R)-(3,5-diethoxy-2-fluoro-phenyl)-[4-(N-hydroxycarbamimidoyl)-phenylamino]-acetic acid ethyl ester.

88. The compound according to claim 1 which is (S)-(3,5-diethoxy-2-fluoro-phenyl)-[4-(N-hydroxycarbamimidoyl)-phenylamino]-acetic acid ethyl ester.

89. The compound according to claim 1 which is (RS)-(3,5-diethoxy-2-fluoro-phenyl)-[4-(N-hydroxycarbamimidoyl)-phenylamino]-acetic acid.

90. The compound according to claim 1 which is (R)-(3,5-diethoxy-2-fluoro-phenyl)-[4-(N-hydroxycarbamimidoyl)-phenylamino]-acetic acid.

91. The compound according to claim 1 which is (S)-(3,5-diethoxy-2-fluoro-phenyl)-[4-(N-hydroxycarbamimidoyl)-phenylamino]-acetic acid.

92. The compound according to claim 1 which is (RS)-[4-(amino-ethoxycarbonylimino-methyl)-phenylamino]-(3,5-diethoxy-2-fluoro-phenyl)-acetic acid ethyl ester.

93. The compound according to claim 1 which is (RS)-{4-[amino-(4-fluoro-phenoxycarbonylimino)-methyl]-phenylamino}-(3,5-diethoxy-2-fluoro-phenyl)-acetic acid ethyl ester.

94. The compound according to claim 1 which is (RS)-{4-[amino-(2,2,2-trichloro-ethoxycarbonylimino)-methyl]-phenylamino}-(3,5-diethoxy-2-fluoro-phenyl)-acetic acid ethyl ester.

95. The compound according to claim 1 which is (RS)-{4-[amino-(5-methyl-2-oxo-[1,3]dioxol-4-ylmethoxycarbonylimino)-methyl]-phenylamino}-(3,5-diethoxy-2-fluoro-phenyl)-acetic acid ethyl ester.

96. The compound according to claim 1 which is (RS)-[4-(amino-methoxycarbonylimino-methyl)-phenylamino]-(3,5-diethoxy-2-fluoro-phenyl)-acetic acid ethyl ester.

97. The compound according to claim 1 which is (RS)-[4-(amino-phenoxycarbonylimino-methyl)-phenylamino]-(3,5-diethoxy-2-fluoro-phenyl)-acetic acid ethyl ester.

98. The compound according to claim 1 which is (RS)-[4-(amino-isobutoxycarbonylimino-methyl)-phenylamino]-(3,5-diethoxy-2-fluoro-phenyl)-acetic acid ethyl ester.

99. The compound according to claim 1 which is (RS)-{4-[amino-(4-fluoro-benzoylimino)-methyl]-phenylamino}-(3,5-diethoxy-2-fluoro-phenyl)-acetic acid ethyl ester.

100. The compound according to claim 1 which is (RS)-(3,5-diethoxy-2-fluoro-phenyl)-[4-(N-hydroxycarbamimidoyl)-phenylamino]-acetic acid butyl ester.

101. The compound according to claim 1 which is (RS)-(3,5-diethoxy-2-fluoro-phenyl)-[4-(N-hydroxycarbamimidoyl)-phenylamino]-acetic acid isopropyl ester.

102. The compound according to claim 1 which is (RS)-[5-ethoxy-2-fluoro-3-[(R)-tetrahydro-furan-3-yloxy]-phenyl]-[4-(N-hydroxycarbamimidoyl)-phenylamino]-acetic acid ethyl ester.

103. The compound according to claim 1 which is (R)-[5-ethoxy-2-fluoro-3-[(R)-tetrahydro-furan-3-yloxy]-phenyl]-[4-(N-hydroxycarbamimidoyl)-phenylamino]-acetic acid ethyl ester.

104. The compound according to claim 1 which is (S)-[5-ethoxy-2-fluoro-3-[(R)-tetrahydro-furan-3-yloxy]-phenyl]-[4-(N-hydroxycarbamimidoyl)-phenylamino]-acetic acid ethyl ester.

105. The compound according to claim 1 which is (RS)-(4-carbamimidoyl-phenylamino)-[5-ethoxy-2-fluoro-3-[(R)-tetrahydro-furan-3-yloxy]-phenyl]-acetic acid ethyl ester hydrochloride.

106. The compound according to claim 1 which is (RS)-(4-carbamimidoyl-phenylamino)-[5-ethoxy-2-fluoro-3-[(R)-tetrahydro-furan-3-yloxy]-phenyl]-acetic acid.

107. The compound according to claim 1 which is (R)-(4-carbamimidoyl-phenylamino)-[5-ethoxy-2-fluoro-3-[(R)-tetrahydro-furan-3-yloxy]-phenyl]-acetic acid.

108. The compound according to claim 1 which is (S)-(4-carbamimidoyl-phenylamino)-[5-ethoxy-2-fluoro-3-[(R)-tetrahydro-furan-3-yloxy]-phenyl]-acetic acid.

109. The compound according to claim 1 which is (RS)-(4-carbamimidoyl-phenylamino)-[5-ethoxy-2-fluoro-3-[(S)-tetrahydro-furan-3-yloxy]phenyl]-acetic acid ethyl ester hydrochloride.

110. The compound according to claim 1 which is (RS)-(4-carbamimidoyl-phenylamino)-[5-ethoxy-2-fluoro-3-[(S)-tetrahydro-furan-3-yloxy]-phenyl]-acetic acid.

111. The compound according to claim 1 which is (R)-(4-carbamimidoyl-phenylamino)-[5-ethoxy-2-fluoro-3-[(S)-tetrahydro-furan-3-yloxy]-phenyl]-acetic acid.

112. The compound according to claim 1 which is (S)-(4-carbamimidoyl-phenylamino)-[5-ethoxy-2-fluoro-3-[(S)-tetrahydro-furan-3-yloxy]-phenyl]-acetic acid.

113. The compound according to claim 1 which is (R)-(4-carbamimidoyl-phenylamino)-[5-ethoxy-2-fluoro-4-(2-hydroxy-ethoxy)-phenyl]-acetic acid.

114. The compound according to claim 1 which is (R)-(4-carbamimidoyl-phenylamino)-(3,5-diethoxy-2-fluoro-phenyl)-acetic acid.

115. The compound according to claim 1 which is (R)-(4-carbamimidoyl-phenylamino)-[5-ethoxy-2-fluoro-3-[(R)-tetrahydro-furan-3-yloxy]-phenyl]-acetic acid.

116. The compound according to claim 1 which is (R)-[5-ethoxy-2-fluoro-4-(2-hydroxy-ethoxy)-phenyl]-[4-(N-hydroxycarbamimidoyl)-phenylamino]-acetic acid ethyl ester.

117. The compound according to claim 1 which is (R)-{4-[amino-(2,2,2-trichloro-ethoxycarbonylimino)-methyl]-phenylamino}-[5-ethoxy-2-fluoro-4-(2-hydroxy-ethoxy)-phenyl]-acetic acid ethyl ester.

118. The compound according to claim 1 which is (R)-[4-(amino-benzoylimino-methyl)-phenylamino]-[5-ethoxy-2-fluoro-4-(2-hydroxy-ethoxy)-phenyl]-acetic acid ethyl ester.

119. The compound according to claim 1 which is (R)-[5-ethoxy-2-fluoro-4-(2-hydroxy-ethoxy)-phenyl]-[4-(N-hydroxycarbamimidoyl)-phenylamino]-acetic acid butyl ester.

120. The compound according to claim 1 which is (R)-[5-ethoxy-2-fluoro-4-(2-hydroxy-ethoxy)-phenyl]-[4-(N-hydroxycarbamimidoyl)-phenylamino]-acetic acid isopropyl ester.

121. The compound according to claim 1 which is (R)-[5-ethoxy-2-fluoro-4-(2-hydroxy-ethoxy)-phenyl]-[4-(N-hydroxycarbamimidoyl)-phenylamino]-acetic acid benzyl ester.

122. The compound according to claim 1 which is (R)-[5-ethoxy-2-fluoro-4-(2-hydroxy-ethoxy)-phenyl]-[4-(N-hydroxycarbamimidoyl)-phenylamino]-acetic acid isobutyl ester.

123. The compound according to claim 1 which is (R)-(4-carbamimidoyl-phenylamino)-[5-ethoxy-2-fluoro-4-(2-hydroxy-ethoxy)-phenyl]-acetic acid ethyl ester.

124. The compound according to claim 1 which is (R)-[5-ethoxy-2-fluoro-4-(2-hydroxy-ethoxy)-phenyl]-[4-(N-hydroxycarbamimidoyl)-phenylamino]-acetic acid.

125. The compound according to claim 1 which is (RS)-[5-ethoxy-2-fluoro-3-[(S)-tetrahydro-furan-3-yloxy]-phenyl]-[4-(N-hydroxycarbamimidoyl)-phenylamino]-acetic acid ethyl ester.

126. The compound according to claim 1, wherein $R^3$ is not alkoxy if $R^5$ is hydrogen.

127. The compound according to claim 1, wherein $R^2$ is hydrogen, alkoxycarbonyloxyalkoxy, or halogenalkoxycarbonyloxyalkoxy.

128. The compound according to claim 1, wherein $R^3$ is hydrogen or heterocycloalkyloxy.

129. The compound according to claim 1, wherein $R^4$ is aryl-alkyl.

130. The compound according to claim 1, wherein $R^5$ is hydroxy, alkoxycarbonyl, halogenalkoxycarbonyl, aryloxycarbonyl, arylalkoxycarbonyl, alkoxyalkoxycarbonyl, cycloalkyloxycarbonyl, alkynyloxycarbonyl, 5-methyl-2-oxo-[1,3]dioxol-4-ylmethoxycarbonyl, arylcarbonyloxy, alkylaminocarbonyloxy, arylaminocarbonyloxy, alkylcarbonyl, arylcarbonyl, heteroarylcarbonyl, or arylaminocarbonyl.

131. The compound according to claim 1, wherein X is Cl, or Br.

132. A compound of the formula:

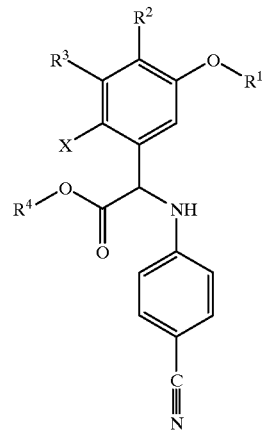

II wherein $R^1$ is alkyl;

$R^2$ is hydrogen, hydroxyalkoxy, alkoxycarbonyloxyalkoxy, or halogenalkoxycarbonyloxyalkoxy;

$R^3$ is hydrogen, alkoxy, or heterocycloalkyloxy;

$R^4$ is hydrogen or the residue of an ester group which is cleavable under physiological conditions; and X is F, Cl, or Br.

* * * * *